United States Patent [19]
Simchowitz et al.

[11] Patent Number: 5,750,354
[45] Date of Patent: May 12, 1998

[54] LIPOXIN TRANSPORT SYSTEM AND USES THEREFOR

[75] Inventors: Louis Simchowitz, St. Louis, Mo.; Charles N. Serhan, Boston, Mass.

[73] Assignee: Brigham and Women's Hospital, Boston, Mass.

[21] Appl. No.: 212,171

[22] Filed: Mar. 11, 1994

[51] Int. Cl.$^6$ ................................................. G01N 33/53
[52] U.S. Cl. ........................... 435/7.24; 435/40.51; 436/71
[58] Field of Search ................................ 435/4, 7.1, 7.2, 435/7.24, 40.51; 436/71, 800, 804

[56] References Cited

PUBLICATIONS

Fiore et al., (1993), "Induction of Functional Lipoxin A$_4$ Receptors in HL–60 Cells", *Cells*, vol. 81, No. 12, pp. 3395–3403.
Fiore et al., (1992), "Lipoxin Recognition Sites", *The Journal of Biological Chemistry*, vol. 267, No. 23, pp. 16168–16176.
Serhan, Charles N., (1991), "Lipoxins: Eicosanoids Carrying Intra– and Intercellular Messages", *Journal of Bioenergetics and Biomembranes*, vol. 23, No. 1, pp. 105–122.
Nicolaou et al., (1991), "Lipoxins and Related Eicosanoids: Biosynthesis, Biological Properties, and Chemical Synthesis", *Angew. Chem. Int. Ed. Engl.*, vol. 30, pp. 1100–1116.
Lefer et al., (1988), "Lipoxins A$_4$ and B$_4$: Comparison of Icosanoids having bronchoconstrictor and vasodilator actions but lacking platelet aggregatory activity", *Proceedings of the National Academy of Sciences*, USA, vol. 85, pp. 8340–8344.
Samuelsson, B., (1987), "An Elucidation of the Arachidonic Acid Cascade Discovery of Prostaglandins, Thromboxane and Leukotrienes", *Drugs*, vol. 33, (Suppl. 1), pp. 2–9.
Simchowitz and Cragoe, (1986), "Regulation of Human Neutrophil Chemotaxis by Intracellular pH", *The Journal of Biological Chemistry*, vol. 261, No. 14, pp. 6492–6500.
Simchowitz, L., (1985), "Intracellular pH Modulates the Generation of Superoxide Radicals by Human Neutrophils", *The Journal of Clinical Investigation*, vol. 76, pp. 1079–1089.
Simchowitz et al, "Canur–Medicated Transport of Lipoxin A$_4$ in Human Neutrophils", Am. J. Physiol 267(6Pt 1) pp. C 1525–1534 Dec. 1994.
Sted Man's Medicare Dictionary °1982 by Waverly Press Inc. p. 1084.

*Primary Examiner*—Marianne P. Allen
*Assistant Examiner*—Patricia A. Duffy
*Attorney, Agent, or Firm*—Lahive & Cockfield, LLP

[57] ABSTRACT

A lipoxin transport system which mediates uptake of lipoxin by cells is disclosed. Lipoxin transport into cells by the lipoxin transport system is inhibitable by 3,5-diiodosalicylic acid (DISA), pentachlorophenol (PCP), $\alpha$-cyano-$\beta$-(1-phenylindol-3-yl)acrylic acid (UK-5099), mersalyl and p-hydroxymercuribenzoate (pHMB). The invention provides methods for identifying inducers, enhancers and inhibitors of the lipoxin transport system. The invention further provides methods for inducing, enhancing or inhibiting lipoxin transport by the lipoxin transport system. Methods for identifying molecules which are transported by the lipoxin transport system, including lipoxin analogs, are also disclosed. Modulation of physiological responses by modulation of lipoxin transport into cells by the lipoxin transport system of the invention are also contemplated.

19 Claims, 8 Drawing Sheets

LIPOXIN TRANSPORT SYSTEM AND USES THEREFOR

GOVERNMENT FUNDING

Work described herein was supported by the Department of Veteran Affairs and by GM-38765 awarded by the National Institutes of Health. The U.S. government therefore may have certain rights in this invention.

BACKGROUND OF THE INVENTION

Lipoxins are a group of biologically active mediators derived from arachidonic acid through the action of lipoxygenase enzyme systems. (Serhan, C. N. and Samuelsson, B. (1984) *Proc. Natl. Acad. Sci. USA* 81:5335). Formation of lipoxins in human cell types is initiated by 5-lipoxygenase or 15-lipoxygenase. (Serhan, C. N. (1991) *J. Bioenerg. Biomembr.* 23:105). Single-cell types generate lipoxins at nanogram levels during human neutrophil-platelet and eosinophil transcellular biosynthesis of eicosanoids. (Serhan, C. N. and Sheppard, K. -A. (1990) *J. Clin. Invest.* 85:772). Lipoxins are conjugated tetraene-containing eicosanoids that modulate cellular events in several organ systems.

The two major lipoxins are lipoxin $A_4$ ($LXA_4$) and lipoxin $B_4$ ($LXB_4$). The lipoxins have been demonstrated to elicit a variety of physiological effects that may play a role in regulating cellular responses involving host defense, vascular tone and inflammation. Lipoxins have a stimulatory effect on certain responses whereas they have an inhibitory effect on other responses. Some effects of the lipoxins include: $LXA_4$ and $LXB_4$, at a concentration of about 10 nM, enhance protein kinase C (PKC) activity in nuclei of erythroleukemia cells (Beckman, B. S. et al. (1992) *Proc. Soc. Exp. Biol. Med.* 201:169); $LXA_4$ and $LXB_4$ at nM levels elicit prompt vasodilation (Busija, D. W. et al. (1989) *Am. J. Physiol.* 256:H468; Katoh, T. et al. (1992) *Am. J. Physiol.* 263 (Renal Fluid Electrolyte Physiol. 32):F436); $LXA_4$ in the $10^{-10}M$ range stimulates cell proliferation in combination with suboptimal concentrations of granulocyte-macrophage colony stimulating factor (GM-CSF) to induce myeloid bone marrow colony formation (Stenke, L. et al. (1991) *Biochem. Biophys. Res. Commun.* 180:255); $LXA_4$ stimulates human mononuclear cell-colony formation (Popov, G. K. et al. (1989) *Bull. Exp. Biol. Med.* 107:93); and $LXA_4$ inhibits chemotaxis of polymorphonuclear leukocytes (Lee, T. H. et al. (1991) *Biochem. Biophys. Res. Commun.* 180:1416.

Lipoxins can act as antagonists to leukotrienes (LT), which are mediators of inflammation. Leukotriene-induced inflanunation occurs, for example, in arthritis, asthma, various types of shock, hypertension, renal diseases, allergic reactions, and circulatory diseases including myocardial infarction. $LXA_4$ modulates $LTC_4$-induced obstruction of airways in asthmatic patients. For example, administration of $LXA_4$ in micromolar amounts via inhalation blocks bronchoconstriction in asthmatic patients. (Christie, P. E. et al. (1992) *Am. Rev. Respir. Dis.* 145:1281). $LXA_4$ inhibits $LTD_4$- and $LTB_4$-mediated inflammation in animal in vivo models. (Badr, K. F. et al (1989) *Proc. Natl. Acad. Sci. USA* 86:3438; Hedqvist, P. et al. (1989) *Acta Physiol. Scand.* 137:571). Prior exposure to $LXA_4$ (nM) blocks renal vasoconstrictor actions of $LTD_4$ (Katoh, T. et al. (1992) *Am. J. Physiol.* 263 (Renal Fluid Electrolyte Physiol. 32) F436). Thus, the vasodilatory effects of lipoxins can counteract vasoconstriction caused by other agents.

The functional effects of lipoxins are mediated, at least in part, through uptake of lipoxins by cells. Specific binding of $LXA_4$ to cell surface $LXA_4$ receptors has been demonstrated. (Fiore, S. et al. (1992) *J. Biol. Chem.* 267:16168–16176; Fiore, S. et al. (1993) *Blood* 81:3395–3403). Additionally, carrier-mediated transport systems for prostaglandins, compounds which are also derived from arachidonic acid, have been characterized in lung, kidney, choroid plexus and retinal epithelium. (Bito, L. Z. et al., (1977) *Am. J. Physiol.* 232:E382–E387; Boumendil-Podevin, E. F. et al., (1985) *Biochim. Biophys. Acta* 812:91–97; Bito, L. Z. et al., (1976) *J. Physiol.* 256:257–271). Identification of a transport system for lipoxins in cells would provide a pathway for lipoxin uptake which could be targeted therapeutically to either inhibit or enhance lipoxin uptake by cells to down- or upregulate physiological responses mediated by lipoxins.

SUMMARY OF THE INVENTION

This invention pertains to methods for inhibiting or enhancing lipoxin uptake by a cell by inhibiting or enhancing the transport of lipoxin into a cell that is mediated by a lipoxin transport system. The invention is based, at least in part, on the discovery of a transport system for lipoxins which is different than, and independent from, binding of lipoxins to specific receptors on a cell. The transport system of the invention has properties of a carrier-mediated transport system. The transport system is inhibitable by anionic inhibitors including 3,5-diiodo-salicylic acid (hereinafter DISA), pentachlorophenol (hereinafter PCP) and α-cyano-β-(1-phenylindol-3-yl)acrylic acid (hereinafter UK-5099) and organo-mercurial agents including mersalyl and p-hydroxymercuribenzoate (hereinafter pHMB). Influx of lipoxin by the transport system is $Na^+$- and membrane voltage-independent but dependent on extracellular pH. For example, transport is inhibited by an alkaline extracellular pH (e.g., pH=8.4) and enhanced by an acidic extracellular pH (e.g., pH=6.4). Inhibitors of the transport system of the invention do not affect binding of lipoxin to specific lipoxin receptors on cells. The characteristics of the transporter system are consistent with an $H^+$+lipoxin cotransport system.

The invention provides a method for identifying an inhibitor of this lipoxin transport system. In the method, a cell, or membrane vesicle thereof, which has the lipoxin transport system is provided. Uptake of a lipoxin by the cell by the lipoxin transport system is characterized by being inhibitable by DISA, PCP, UK-5099, mersalyl or pHMB. The cell is contacted with a labeled lipoxin in the presence of a molecule to be tested, uptake of labeled lipoxin by the cell is measured and the ability of the molecule to inhibit uptake of labeled lipoxin by the cell is determined. An inhibitor of a lipoxin transport system is identified by the ability of the molecule to inhibit uptake of labeled lipoxin by the cell by the lipoxin transport system. Preferably, the labeled lipoxin is $LXA_4$. In preferred embodiments, the cell is a neutrophil or differentiated HL-60 cell.

The invention further provides a method for inhibiting transport of a lipoxin into a cell which has a lipoxin transport system. The method comprises contacting the cell with a molecule which is an inhibitor of the lipoxin transport system. In preferred embodiments, the inhibitor is an anion or organomercurial agent. An inhibitor of the lipoxin transport system can also be used to regulate lipoxin-mediated responses in a cell which has a lipoxin transport system by contacting the cell with the inhibitor. For example, an inhibitor of the lipoxin transport system can be used to down-regulate a response which is stimulated by a lipoxin by preventing transport of the lipoxin into a cell.

Alternatively, an inhibitor of the lipoxin transport system can be used to up-regulate a response which is inhibited by a lipoxin by preventing uptake of the lipoxin by the cell.

The invention further provides a method for identifying a molecule which induces or enhances lipoxin transport by a lipoxin transport system. The method includes providing a cell, or membrane vesicle thereof, which has a lipoxin transport system or in which a lipoxin transport system can be induced. The cell is contacted with a labeled lipoxin in the presence of a molecule to be tested, uptake of labeled lipoxin by the cell is measured and the ability of the molecule to induce or enhance uptake of labeled lipoxin by the cell is determined. A molecule which induces or enhances lipoxin transport by a lipoxin transport system is identified based upon this ability. Preferably, the labeled lipoxin is $LXA_4$ and the cell is a neutrophil or differentiated HL-60 cell.

The invention also provides a method for identifying a lipoxin analog which is transported at a faster rate than a natural lipoxin by a lipoxin transport system. The method includes providing a cell, or membrane vesicle thereof, which has a lipoxin transport system, contacting the cell with a labeled lipoxin analog to be tested, measuring the rate of uptake of the lipoxin analog by the cell, and comparing the rate of uptake of the lipoxin analog by the cell to the rate of uptake of a natural lipoxin by the cell to identify a lipoxin analog which is transported at a faster rate than a natural lipoxin by a lipoxin transport system.

The invention still further provides a method for enhancing transport of a lipoxin into a cell which has a lipoxin transport system. The method comprises contacting the cell with a molecule which enhances transport of a lipoxin by the lipoxin transport system. For example, n-formyl-methionyl-leucyl-phenylalanine and phorbol myristate acetate can enhance uptake of lipoxin by the lipoxin transport system. An enhancer of the lipoxin transport system can also be used to modulate lipoxin-mediated responses in a cell which has a lipoxin transport system by contacting the cell with the enhancer. For example, an enhancer of the lipoxin transport system can be used to up-regulate a response which is stimulated by a lipoxin by increasing transport of the lipoxin into a cell. Alternatively, an enhancer of the lipoxin transport system can be used to down-regulate a response which is inhibited by a lipoxin by increasing uptake of the lipoxin by the cell.

DETAILED DESCRIPTION OF THE INVENTION

Figure 1:
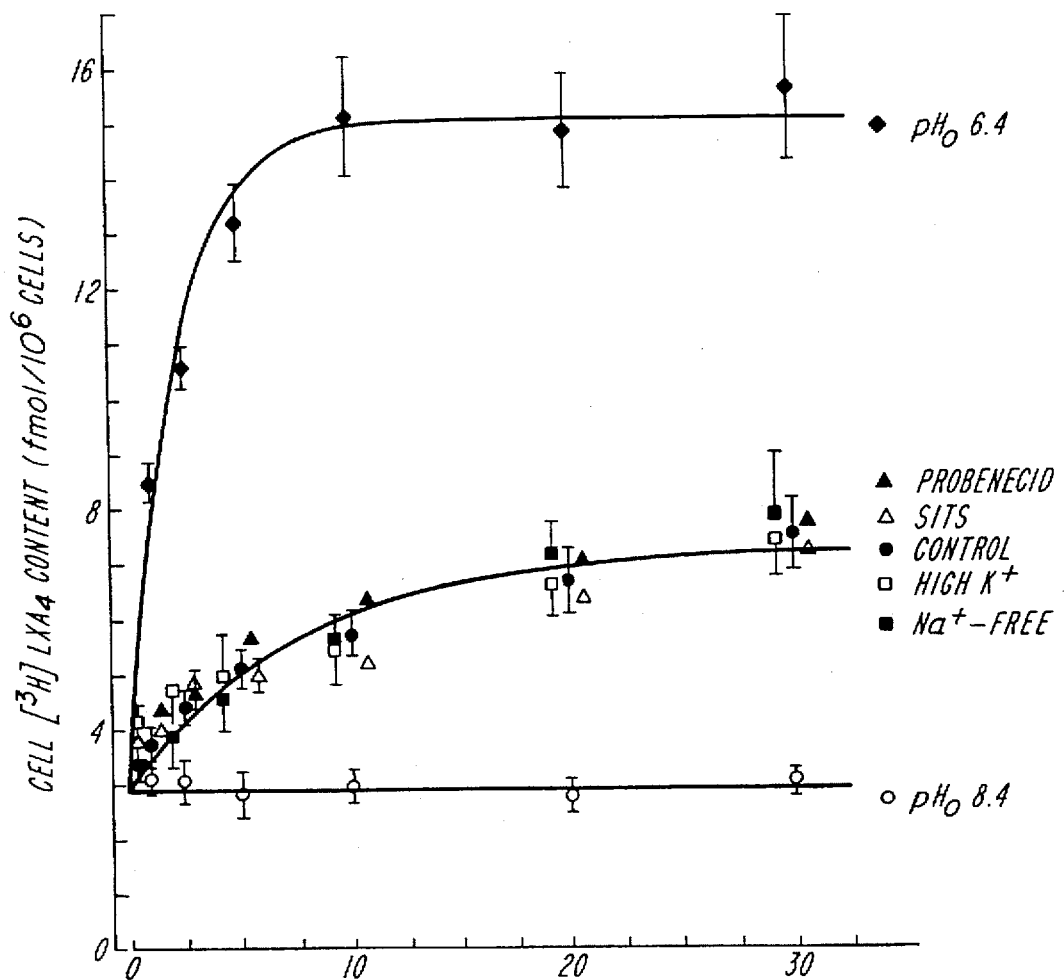
FIG. 1 is a graph depicting the time couse of [$^3$H]$LXA_4$ influx into neutrophils in the presence of medium alone, probenecid, SITS, $Na^+$-free medium, high $K^+$ medium, medium at pH 6.4 and medium at pH 8.4.

This invention relates to lipoxin uptake by a cell via a lipoxin transport system. The invention is based, at least in part, on the discovery of a transport system in cells which promotes uptake of lipoxin by the cells. The lipoxin transport system has properties of a carrier-mediated transport system. Influx of lipoxin into cells by the lipoxin transport system is sensitive to certain anionic inhibitors such as 3,5-diiodo-salicylic acid (DISA), pentachlorophenol (PCP) and α-cyano-β-(1-phenylindol-3-yl)acrylic acid (UK-5099), and certain organomercurial (and sulfhydryl-reactive) agents such as mersalyl and p-hydroxymercuribenzoate (pHMB). Influx of lipoxin by the transport system also exhibits a dependence on pH (pK'5.9) but is independent of membrane voltage and $Na^+$ concentration. These properties of the transport system are consistent with an $H^+$+lipoxin cotransport system. Some cell types are also known to have specific receptors for lipoxins. Inhibitors of the lipoxin transport system do not affect binding of lipoxin to specific lipoxin receptors on cells. Thus, the lipoxin transport system of the invention represents a distinct pathway for lipoxin uptake which is different from and independent of binding of lipoxin to specific lipoxin receptors. This transport pathway can serve as a target for intervention in order to increase or decrease uptake of lipoxin by a cell. Modulating lipoxin uptake provides a means by which to up- or downregulate physiological responses mediated by lipoxins.

A. Properties of the Lipoxin Transport System

The lipoxin transport system of the invention has several characteristics which can be used to identify the presence of the transport system on a particular cell and distinguish the transport system from binding of lipoxin to specific receptors. The primary characteristic utilized to identify lipoxin transport mediated by the lipoxin transport system is the ability of certain inhibitors to inhibit lipoxin transport by this system. A lipoxin transport system can be identified on a cell by incubating the cell with a lipoxin (e.g. $LXA_4$) which is labeled with a detectable substance (e.g. radioactively labeled), measuring the uptake of lipoxin by the cell land examining the effect of certain inhibitors and/or conditions on uptake of lipoxin by the cell to determine whether uptake is mediated by the lipoxin transport system. For example, a cell can be incubated with $^3$H-$LXA_4$ and uptake of lipoxin by the cell can be determined by measuring the association of the radiolabel with the cell over time. Association of lipoxin with the cell could be due to binding of lipoxin to specific receptors on the cell, transporter-mediated uptake of the lipoxin or a combination of the two mechanisms. To determine the amount of lipoxin uptake which is transporter-mediated, the cell is incubated with both labeled lipoxin and an inhibitor of the lipoxin transport system. For example, the cell can be incubated with $^3$H-LXA$_4$ and DISA. Alternatively, an inhibitor selected from PCP, UK-5099, mersalyl and pHMB can be used. Association of lipoxin with the cell which is due to binding of lipoxin to specific receptors is unaffected by the presence of these inhibitors and thus will still be detectable. However, association of lipoxin with the cell which is due to uptake of lipoxin by the lipoxin transport system is inhibited by these inhibitors and thus will be decreased or eliminated. By comparing the amount of lipoxin which associates with the cell in the presence and in the absence of DISA (or another appropriate inhibitor), uptake of lipoxin via the lipoxin transport system can be determined.

The effect of certain conditions on association of lipoxin with the cell can also be used to identify transporter-mediated uptake of lipoxin by the cell. For example, transporter-mediated uptake is increased by lowering the extracellular pH to 6.4, whereas it is decreased by raising the extracellular pH to 8.4. Binding of lipoxin to specific receptors is not affected by such pH variations. Thus, a cell can be incubated with a labeled lipoxin (e.g. $^3$H-LXA$_4$) and the effect of varying the extracellular pH on association of the lipoxin with cell can be determined as an indicator of the presence or absence of a lipoxin transport system in the cell.

Additionally, certain compounds which enhance uptake of lipoxin by a cell via the lipoxin transport system have been identified. For example, n-formyl-methionyl-leucylphenylalanine (FMLP) and phorbol myristate acetate (PMA) can increase the initial rate of lipoxin influx into a cell by the lipoxin transport system. Thus, a cell can be incubated with a labeled lipoxin (e.g. $^3$H-LXA$_4$) and the effect of FMLP or PMA on association of the lipoxin with cell can be determined. Increased uptake of lipoxin in the presence of FMLP or PMA can be used as an additional indicator of the presence of a lipoxin transport system in the cell.

In contrast, other conditions and compounds have little or no effect on the lipoxin transport system. Transporter-mediated uptake is not affected by removing extracellular Na$^+$ or by raising extracellular K$^+$ (which depolarizes membrane voltage). Additionally, transporter-mediated uptake is not inhibited by probenecid or the disulfonic stilbene SITS, two general inhibitors of anion transport. Several sulfhydryl-reactive compounds also do not inhibit transporter-mediated uptake including NEM, iodoacetate and 2,2'-dithiobispyridine (hereinafter 2,2'-DTBP), whereas the sulfhydryl-reactive compounds 7-chloro-4-nitrobenz-2-oxa-1,3-diazole (hereinafter NBD-Cl) and eosin-5-maleimide cause only modest inhibition (approximately 20%). The lack of (or minimal) effect of these conditions or compounds on lipoxin uptake by a cell can be used as additional indicators that the uptake occurs by a lipoxin transport system.

The lipoxin transport system displays other characteristics which can be utilized as additional indicators of lipoxin transport by this system. For example, the inhibitor profile of the lipoxin transport system distinguishes it from several other known specialized anion transport systems. These systems include a Cl$^-$/HCO$_3^-$ exchanger, a sulfate carrier and an H$^+$ +lactate$^-$ cotransporter. For example, the Cl$^-$/HCO$_3^{-31}$ exchanger is resistant to pHMB whereas the lipoxin transporter is inhibited by pHMB and, additionally, the Cl$^-$/HCO$_3^-$ exchanger displays a pH-dependence opposite to that for lipoxin influx (Simchowitz, L. et al., (1991) *Am. J. Physiol.* 261:C906–C915). The sulfate carrier is very sensitive to the disulfonic stilbene SITS and to probenecid (Simchowitz, L. and Davis, A. O., (1989) *J. Gen. Physiol* 94:95–124) while lipoxin uptake is not. Lactic acid fluxes are completely blocked by NEM and NBD-CL (Simchowitz, L. and Vogt, S. K. (1993) *J. Membr. Biol.* 131:23–34) while those of lipoxin are not. Also, the lipoxin transport system displays substrate specificity in that not all arachidonic acid derivatives are transported by the system. For example, arachidonic acid, prostaglandin E$_2$ (hereinafter PGE$_2$), 15-HETE, and the leukotrienes B$_4$, C$_4$ and D$_4$ are not transported by the lipoxin transport system. Furthermore, methyl ester derivatives of lipoxins can enter cells by non-ionic diffusion, thus bypassing the lipoxin transport system. Because of the ester linkage through the carboxyl group, the lipoxin methyl ester derivative is uncharged and therefore lipophilic. Thus, the methyl ester derivative can permeate cells by simple diffusion whereas the lipoxin free acid cannot. Inhibitors which block transporter-mediated uptake of lipoxins do not affect entry of methyl ester derivatives of lipoxins into the cell.

When assaying a cell for the presence of a lipoxin transport system, conditions can be chosen which promote measurement of transporter-mediated lipoxin uptake while reducing the contribution of lipoxin receptor binding to the observed association of lipoxin with the cell. That is, a concentration of labeled lipoxin can be chosen which rapidly saturates binding of the lipoxin to specific lipoxin receptors. Under this condition, lipoxin uptake by the cell which occurs subsequent to saturation of the specific receptors should be exclusively due to transporter-mediated uptake, which can be confirmed by examining the sensitivity of this uptake to DISA or other inhibitors. A concentration of lipoxin can be chosen based upon the K$_d$ of receptor binding. For example, the binding of $^3$H-LXA$_4$ to specific receptors has been found to have a K$_d$ of 0.5±0.3 nM. A concentration of at least about 10-fold greater than the K$_d$, e.g., 5 nM, can be used to saturate receptor binding. Preferably, a concentration of at least about 100-fold greater than the K$_d$, e.g. 50 nM, is used to saturate receptor binding. At these concentrations, binding of the lipoxin to specific receptors is rapidly saturated, i.e., is saturated within about 1 minute after incubating the lipoxin with a cell expressing lipoxin receptors. One can continue to measure the association of lipoxin with the cell over time, e.g., at 10 min., 20 min. and 30 min. post-incubation. Uptake of lipoxin by the transport system is not saturated under these conditions and thus additional accumulation of lipoxin within the cell due to transporter-mediated uptake can be measured.

In addition to identifying a cell that has a lipoxin transport system, by the aforementioned procedures, the rate of uptake of lipoxin by the cell via the lipoxin transport system can be determined by measuring the uptake of lipoxin by the cell over time, wherein the uptake is inhibitable by DISA or another inhibitor (e.g., PCP, UK-5099, mersalyl or pHMB). This rate determination is described in detail in the Examples. Influx of LXA$_4$ into neutrophils by the lipoxin transport system has been found to occur at a rate of about 0.6 fmol/10$^6$ cells/min.

B. Identification of Molecules that Inhibit or Enhance Lipoxin Transport

A cell which has a lipoxin transport system can be used to screen molecules for their ability to inhibit or enhance lipoxin uptake by the lipoxin transport system. The invention provides a method for identifying a molecule which is an inhibitor of a lipoxin transport system. In the first step of the method, a cell, or membrane vesicle thereof, which has a lipoxin transport system is provided. A whole intact cell can be used or a membrane vesicle which contains the lipoxin transport system can be used. The cell or membrane vesicle containing the lipoxin transport system allow for the transfer of a lipoxin from an extracellular site to an intracellular or intravesicular site, which can be measured. Membrane vesicles can be prepared from intact cells by standard procedures known in the art. The term "lipoxin transport system" is used herein to describe a system in which transport of a lipoxin by the system is inhibitable by a compound selected from a group consisting of DISA, PCP, UK-5099, mersalyl and pHMB. The cell (or membrane vesicle) which is provided may also have specific lipoxin receptors. However, binding of lipoxin to these receptors is not inhibitable by DISA, PCP, UK-509, mersalyl or pHMB.

The cell, or membrane vesicle, thereof, is then contacted with a labeled lipoxin in the presence of a molecule to be tested. The term "labeled lipoxin" is used herein to describe a lipoxin which is labeled with a detectable substance. Preferably, the detectable substance is a radioactive isotope. For example, a lipoxin can be labeled with $^3$H. Alternatively, a lipoxin could be labeled with $^{14}$C. Alternative detectable substances include fluorescent and luminescent materials. The requirements for the detectable substance include that it must not interfere with uptake of the lipoxin by the lipoxin transport system and it must allow measurement of association of the labeled lipoxin with the cell.

After contacting the cell, or membrane vesicle thereof, with the labeled lipoxin, uptake of the labeled lipoxin is measured. This can be accomplished by measuring the amount of the detectable substance (e.g., the radiolabel) which is specifically associated with the cell. For example, at various intervals post-incubation, an aliquot of the cells can be separated from the incubation medium and the cell-associated label (e.g. amount of radiolabel present in the cell pellet) can be measured.

A molecule which is an inhibitor of a lipoxin transport system can be identified by its ability to inhibit uptake of a labeled lipoxin by a cell, wherein the uptake is also inhibitable by DISA, PCP, UK-5099, mersalyl or pHMB. The lipoxin uptake defined in this way excludes lipoxin uptake by a cell which is due to binding of lipoxin to specific receptors. The amount and/or rate of lipoxin transport which is inhibitable by DISA or another inhibitor can be predetermined for the cell to be used in the method by the procedures described earlier. For example, in a preferred embodiment the cell used in the method is a neutrophil, which has both lipoxin specific receptors and a lipoxin transport system. In the presence of 5 nM $LXA_4$, about 3 fmol $LXA_4/10^6$ cells becomes associated with neutrophils within 1 minute due to binding to specific lipoxin receptors, whereupon the receptors become saturated. Transport-mediated uptake of $LXA_4$ by neutrophils continues to occur at a rate of about 0.6 fmol/$10^6$ cells/minute above that due to specific binding to receptors. When incubated in the presence of 0.5 mM DISA, this additional (i.e., 0.6 fmol/$10^6$ cells/minute) $LXA_4$ influx is blocked, whereas the initial association of $LXA_4$ due to receptor binding (3 fmol/$10^6$ cells) is still detectable. An inhibitor of a lipoxin transport system can therefore be identified using neutrophils by identifying a molecule which blocks the additional 0.6 fmol/$10^6$ cells/minute influx of lipoxin into the cells above that due to receptor binding. Thus, this method provides a way to identify molecules which specifically inhibit only one of two possible routes of entry of lipoxin into a cell.

In another embodiment, the cell used in the method is a differentiated HL-60 cell (or membrane vesicle thereof). HL-60 cells which have been stimulated to differentiate by exposure to retinoic acid (which induces a neutrophil-like morphology) have been found to express the lipoxin transport system upon differentiation. Other stimuli which induce HL-60 cells to differentiate to a neutrophil-like morphology include dibutyryl-cAMP and dimethyl sulfoxide and it is likely that these stimuli can also be used to induce the lipoxin transport system on HL-60 cells. The lipoxin transport system has not been found to be present on unstimulated human erythrocytes, lymphocytes and platelets and thus these cell types are not preferred for use in this method. However, acquisition of such a transport system could arise after exposure of resting cells to appropriate stimuli or activating agents. Other cell types which possess the lipoxin transport system or which, upon stimulation, are induced to express the lipoxin transport system can be identified by procedures described earlier based upon the properties of the transport system. Such cells can then be used to identify inhibitors of lipoxin uptake by the lipoxin transport system.

The specificity of an inhibitor identified according to the method of the invention can be further determined by utilizing the known properties of the lipoxin transport system. For example, an inhibitor specific for the transport system would not affect entry of molecules into the cell by non-ionic diff-usion. Accordingly, the inhibitor would not affect uptake of a lipoxin methyl ester derivative by the cell. The inhibitor might inhibit uptake of other molecules by other transport systems (e.g., the anionic inhibitors DISA, PCP, UK-5099 and mersalyl are known to also block other transport systems such as the $Cl^-/HCO_{3-}$ and the $H^+$+lactate$^-$ cotransporter). Alternatively, an inhibitor might be specific for the lipoxin transport system and not affect the activity of other anion transport systems having a different substrate specificity. In this case, for example, the inhibitor would not affect transport by a $Cl^-/HCO_{3-}$ exchanger, a sulfate carrier or an $H^+$+lactate$^-$ cotransporter present in the cell.

Similar to the method for identifying a molecule which is an inhibitor of a lipoxin transport system, the invention provides a method for identifying a molecule which enhances transport of lipoxin by a lipoxin transport system or which induces the expression of the transport system on cells which do not constitutively possess it. The method involves providing a cell (or membrane vesicle thereof) which has a lipoxin transport system (e.g., neutrophils) or which does not have a lipoxin transport system constitutively but in which the transport system can be induced (e.g., HL-60 cells). The cell is contacted with a labeled lipoxin in the presence of a molecule to be tested, uptake of the lipoxin by the cell is measured and the ability of the molecule to enhance or induce uptake of lipoxin by the cell is determined. A molecule which enhances or induces uptake of lipoxin by the cell by the lipoxin transport system can be identified based upon this ability. As described earlier, lipoxin uptake by a lipoxin transport system is defined herein as lipoxin transport which is inhibitable by DISA, PCP, UK-5099, mersalyl or pHMB, thereby excluding lipoxin uptake mediated by specific receptors.

The ability of a molecule to induce or enhance lipoxin uptake by the lipoxin transport system is determined by comparing the amount and/or rate of uptake of lipoxin in the presence of the molecule tested to a predetermined amount and/or rate of lipoxin influx into the cell by the lipoxin transport system in the absence of the molecule tested. For example, in a preferred embodiment the cell used in the method is a neutrophil, which has a lipoxin influx rate due to transporter-mediated uptake of about 0.6 fmol/$10^6$ cells/minute. In the presence of a molecule which enhances transport of lipoxin by a lipoxin transport system, the transporter-mediated influx of lipoxin into neutrophils would be greater than 0.6 fmol/$10^6$ cells/minute. Alternatively, a cell which does not transport lipoxin in the absence of a molecule to be tested can be used to identify an inducer of lipoxin transport. In this case, the rate of transport of lipoxin by the lipoxin transport system in the absence of an inducer molecule would be 0 fmol/$10^6$ cells/minute and in the presence of an inducer molecule would be greater than 0 fmol/$10^6$ cells/minute.

In another embodiment, the cell used to identify a molecule which induces or enhances lipoxin transport by a lipoxin transport system is an HL-60 cell (or membrane vesicle thereof). For example, when HL-60 cells are differentiated (e.g., by treatment with retinoic acid) they express the lipoxin transport system. Thus, differentiated HL-60 cells can be used to identify an enhancer of the lipoxin transport system. Alternatively, in an undifferentiated state, HL-60 cells do not express the lipoxin transport system but can be induced to express the system. Thus, undifferentiated HL-60 cells can be used to identify an inducer of a lipoxin transport system. The lipoxin transport system has not been found to be present on unstimulated human erythrocytes, lymphocytes and platelets and thus these cell types are not preferred for identifying an enhancer of the transport system. However, these or other cell types can be stimulated with a molecule to determine whether the moelcule induces lipoxin transport by the lipoxin transport system. Other cell types which possess the lipoxin transport system can be identified by procedures described earlier based upon the properties of the transport system and used to identify enhancers of lipoxin transport.

Lipoxin uptake by mechanisms other than the lipoxin transport system, e.g. binding of lipoxin to specific lipoxin receptors and non-ionic diffusion of methyl ester lipoxin derivatives into a cell, would not be affected by molecules which specifically induce or enhance lipoxin transport by the lipoxin transport system. The specificity of an inducer or enhancer of the lipoxin transport system can be determined by measuring the binding of labeled lipoxin to specific receptors (i.e., the DISA-insensitive component of lipoxin uptake by the cell) or the uptake of labeled lipoxin methyl ester by the cell in the presence and absence of the molecule.

C. Inhibiting or Enhancing Lipoxin Transport by a Lipoxin Transport System

The lipoxin transport system of the invention provides a pathway for lipoxin entry into a cell which can be targeted in order to increase or decrease lipoxin uptake by the cell. Accordingly, the invention provides a method for inhibiting uptake of a lipoxin by a cell which has a lipoxin transport system comprising contacting the cell with a molecule which is an inhibitor of the lipoxin transport system. In one embodiment, the inhibitor of the lipoxin transport system is a weak organic acid (pK'4-6) so that at physiological pH it exists predominantly as an anion. Examples of anionic compounds which can inhibit uptake of lipoxin by the lipoxin transport system include DISA, PCP and UK-5099. Certain anionic compounds do not inhibit lipoxin transport by the lipoxin transport system. These compounds include probenecid and disulfonic stilbene SITS. In another embodiment, the inhibitor of the lipoxin transport system is an organomercurial agent. Examples of organomercurial agents which can inhibit uptake of lipoxin by the lipoxin transport system include mersalyl and pHMB. Certain other sulfhydryl-reactive compounds (which includes the organomercurial agents) do not inhibit transporter-mediated uptake. These compounds include NEM, iodoacetate and 2,2'-DTBP. Additional compounds which can inhibit lipoxin uptake by the lipoxin transport system are diphenylamine-2-carboxylate and niflumate. Other compounds which can inhibit uptake of lipoxin by the lipoxin transport system can be identified by the aforementioned method for identifying such molecules.

Once identified, a molecule which is an inhibitor of a lipoxin transport system can be used to inhibit lipoxin uptake by a cell by contacting the molecule with a cell which has a lipoxin transport system. The term "contacting" as used herein is intended to include incubating a cell with a molecule in vitro, e.g., adding the molecule to a medium containing the cell in vitro, and exposing the cell to the molecule in vivo, e.g., administering the molecule in vivo by a route such that the cell will be contacted by the molecule. The term "contacting" is also intended to include other possible methods of introducing a molecule into a cell, such as by transfection (e.g., of nucleic acid molecules), microinjection, liposome-mediated transfer etc. which result in uptake of the molecule by the cell. Non-limiting inhibitory concentrations for known inhibitor molecules are as follows (expressed as $K_{0.5}$, the concentration at which 50% of lipoxin transport is inhibited): DISA-12 µM; PCP-25 µM; and mersalyl-110 µM.

A cell which has both a lipoxin transport system and specific lipoxin receptors can be contacted with a molecule which inhibits lipoxin uptake by the lipoxin transport system to specifically inhibit entry of lipoxin into the cell via this pathway while not affecting entry of lipoxin into the cell via specific receptors. Blocking of the transport-mediated pathway for lipoxin uptake while preserving the function of the receptor-mediated pathway for lipoxin uptake can be useful for specifically interfering with lipoxin-mediated responses which are stimulated through the transport pathway while maintaining lipoxin-mediated responses which are stimulated through binding of lipoxin to specific receptors. Alternatively, it may be desirable to inhibit lipoxin entry into cells by both mechanisms (i.e., transporter-mediated and receptor-mediated) in order to interfere with lipoxin-mediated responses involving both pathways. Accordingly, a cell can be contacted both with a molecule which inhibits lipoxin uptake by the lipoxin transport system and with a molecule which inhibits binding of lipoxin to specific lipoxin receptors.

The invention further provides a method for inducing or enhancing transport of a lipoxin into a cell which has a lipoxin transport system comprising contacting the cell with a molecule which induces or enhances transport of a lipoxin by the lipoxin transport system. For example, certain molecules have been identified which increase the initial rate of uptake of lipoxin by neutrophils by the lipoxin transport system. These molecules, which can thus function as enhancers of lipoxin transport, include n-formyl-methionyl-leucyl-phenylalanine (FMLP), phorbol myristate acetate (PMA) and the cationic ionophore A23187. Accordingly, a cell (e.g., a neutrophil) can be contacted with FMLP, PMA or A23187 to enhance uptake of lipoxin by the cell by the lipoxin transport system. Other compounds which can induce or enhance uptake of lipoxin by the lipoxin transport system can be identified by the aforementioned method for identifying such molecules. Once identified, a molecule which is an inducer or enhancer of a lipoxin transport system can be used to induce or enhance lipoxin uptake by a cell by contacting the molecule with a cell which has a lipoxin transport system or in which a lipoxin transport system can be induced.

D. Other Substrates for the Lipoxin Transport System

The lipoxin transport system of the invention exhibits substrate specificity in that it does not transport certain other arachidonic acid derivatives such as $PGE_2$, 15-HETE, $LTB_4$, $LTC_4$ or $LTD_4$ to the same degree as it transports lipoxins (see Example 6). There is also evidence that the lipoxin transport system exhibits stereospecificity in that the 11-transcontaining isomer of $LXA_4$ is transported at about a 3-fold lower rate relative to the native 11-cis-containing $LXA_4$.

The ability of a compound to be transported by the lipoxin transport system (i.e., to be a substrate for the system) can be determined directly by labeling a molecule to be tested with a detectable substance, contacting a cell having a lipoxin transport system with the labeled molecule and measuring uptake of the labeled molecule by the lipoxin transport system. That the molecule is transported by the lipoxin transport system is determined based upon the known properties of the lipoxin transport system, such as inhibition of transport by DISA, PCP, UK-5099, mersalyl or pHMB, and/or other additional distinguishing characteristics as described in Section A.

The ability of a compound to be transported by the lipoxin transport system (i.e., to be a substrate for the system) can also be determined based upon its ability to competitively inhibit uptake of a labeled lipoxin by the lipoxin transport system (i.e., can act as a competing substrate), thereby reducing transport of the labeled lipoxin by the transport system when both the test compound and the labeled lipoxin are incubated with a cell having a lipoxin transport system. For example, a test compound and a radiolabeled $LXA_4$ can be incubated with neutrophils and the amount and/or rate of uptake of the radiolabeled $LXA_4$ by the cells in the presence of the test compound can be compared with the amount and/or rate of uptake of the radiolabeled $LXA_4$ by the cells in the absence of the test compound. A compound which is also transported by the lipoxin transport system will compete with the radiolabeled $LXA_4$ for transporter-mediated uptake, thereby reducing the uptake of the radiolabeled $LXA_4$.

In a preferred embodiment, a compound which can act as a substrate for the lipoxin transport system is a lipoxin analog of a natural lipoxin. The term "lipoxin analog" as used herein is intended to include any compound which binds a lipoxin receptor recognition site or binds a macromolecule or complex of macromolecules, including an enzyme and its cofactor, which is bound by a lipoxin. Lipoxin analogs include compounds which are structurally similar to a natural lipoxin, compounds which share the same receptor recognition site, compounds which share the same or similar lipoxin metabolic transformation region as lipoxin, and compounds which are art-recognized as being analogs of lipoxin. Lipoxin analogs include lipoxin analog metabolites. Lipoxin analogs include compounds such as those described in U.S. patent application Ser. No. 08/077,300 by C. N. Serhan, which is hereby incorporated by reference. The term "lipoxin analog" is further understood to encompass compounds containing radioactive isotopes, such as but not limited to tritium ($^3H$), deuterium ($^2H$), carbon ($^{14}C$), or otherwise. The lipoxin analog can be radiolabeled or derivatized, for example to determine their uptake by a lipoxin transport system. Lipoxin analogs can also be labeled with other detectable substances, such as fluorescent labels. The term "natural lipoxin" as used herein is intended to refer to a naturally-occurring lipoxin or lipoxin metabolite. Where an analog has activity for a lipoxin-specific receptor, the natural lipoxin is the normal ligand for that receptor. For example, where an analog is a $LXA_4$ analog having specific activity for a $LXA_4$ specific receptor on differentiated HL-60 cells, the corresponding lipoxin is $LXA_4$. Where an analog has activity as an antagonist to another compound (such as a leukotriene), which is antagonized by a naturally-occurring lipoxin, that lipoxin is the corresponding natural lipoxin.

Nonlimiting examples of the structures and syntheses of both lipoxins and lipoxin analogs are illustrated in the following patents and publications: Nicolaou, K. C. et al. (1989). *Biochim. Biophys. Acta* 1003:44–53; Nicolaou, K. C. et al. (1989). *J. Org. Chem.* 54: 5527–5535; Nicolaou, K. C. et al.(1991). *Angew. Chem. Int. Ed. Engl.* 30: 1100–1116; U.S. Pat. Nos. 4,576,758; 4,560,514; 5,079261; and 5,049,681; and JP Patent Nos. 3,227,922; 63,088,153; 62,198,677; and 1,228,994. Methods of making lipoxin analogs which have longer tissue half-lives than the corresponding natural lipoxin are illustrated in the Serhan, C. N., U.S. patent application entitled "Lipoxin Analogs," Ser. No. 08/077,300 (cited supra). Analogs may also be synthesized by a person of ordinary skill using the well-known methods of eicosanoid synthesis illustrated in the cited references.

The invention provides a method for identifying a lipoxin analog which is transported by a lipoxin transport system. The method involves providing a cell (or membrane vesicle thereof) which has a lipoxin transport system, contacting the cell with a lipoxin analog to be tested together with a labeled natural lipoxin which is transported by the lipoxin transport system, measuring the rate of uptake of the labeled natural lipoxin by the cell, determining the ability of the natural lipoxin to competitively inhibit uptake of the natural lipoxin, said uptake being inhibitable by DISA, PCP, UK-5099, mersalyl or pHMB, and identifying a lipoxin analog which is transported by a lipoxin transport system by the ability of the lipoxin analog to competitively inhibit uptake of the natural lipoxin by the lipoxin transport system. Preferred cells, or membrane vesicles thereof, for use in the method are neutrophils and differentiated HL-60 cells, or membrane vesicles thereof. For example, neutrophils are incubated with a lipoxin analog and a radiolabeled natural lipoxin (e.g. $^3H$-$LXA_4$) and uptake of the labeled natural lipoxin by the neutrophils is assessed by measuring the cell-associated radiolabel over time. The amount and/or rate of uptake of the labeled natural lipoxin in the presence of the lipoxin analog is compared to a predetermined amount and/or rate of uptake of the natural lipoxin by the cells in the absence of the lipoxin analog (determined by procedures described earlier). A lipoxin analog which is transported by a lipoxin transport system is identified based upon the ability of the lipoxin analog to competitively inhibit (i.e., decrease) uptake of the natural lipoxin by the lipoxin transport system (i.e., uptake which is inhibitable by DISA, PCP, UK-5099, mersalyl or pHMB). For example, transporter-mediated uptake of the natural lipoxin $LXA_4$ by neutrophils is known to occur at a rate of about 0.6 $fmol/10^6$ cells/minute above that due to specific receptor binding in the absence of a lipoxin analog. In the presence of a lipoxin analog which is transported by a lipoxin transport system, transporter-mediated uptake of natural lipoxin $A_4$ by neutrophils is at a rate lower than about 0.6 $fmol/10^6$ cells/minute.

Additionally, uptake of a lipoxin analog by the lipoxin transport system can be assessed directly using a labeled lipoxin analog. Accordingly, an alternative method for identifying a lipoxin analog which is transported by a lipoxin transport system involves providing a cell with a lipoxin transport system, contacting the cell with a lipoxin analog which is labeled (e.g., radiolabeled), measuring uptake of the labeled lipoxin analog by the lipoxin transport system, wherein said uptake is inhibitable by DISA, PCP, UK-5099, mersalyl or pHMB, and identifying a lipoxin analog which is transported by a lipoxin transport system by the uptake of the lipoxin analog. The rate of uptake of a lipoxin analog can be determined (as described in the Examples) and a lipoxin analog which is transported at a faster rate than a natural lipoxin by a lipoxin transport system can be identified. For example, a lipoxin analog which is transported at a faster rate than a natural lipoxin by neutrophils can be identified by the uptake of the lipoxin analog by neutrophils at a rate greater than about 0.6 fmol/$10^6$ cells/minute.

E. Modulating Lipoxin-Mediated Responses

Lipoxins are known to regulate a variety of biochemical and physiological events, including events involved in cell activation, signal transduction and stimulus-response coupling (see for example Samuelsson, et al. (1987) *Science* 237:1171–1176). Modulating the function of the lipoxin transport system of the invention provides a means by which to upregulate or downregulate lipoxin-mediated responses through increasing or decreasing uptake of lipoxins by a cell via the lipoxin transport system.

Molecules which inhibit, enhance or induce uptake of lipoxins by the lipoxin transport system can be used to modulate lipoxin-mediated responses. For example, an inhibitor of a lipoxin transport system can be used to increase or decrease a physiological response, depending upon whether uptake of a lipoxin by the transport system stimulates or inhibits the particular response. For example, a physiological response by a cell which is increased by uptake of a lipoxin by the lipoxin transport system can be decreased by contacting the cell with an inhibitor of the lipoxin transport system to decrease lipoxin uptake by the cell. Alternatively, a physiological response which is decreased by uptake of a lipoxin by the lipoxin transport system can be increased by contacting the cell with an inhibitor of the lipoxin transport system to decrease lipoxin uptake by the cell. Likewise, an inducer or an enhancer of a lipoxin transport system can be used to increase or decrease physiological responses, depending upon whether uptake of a lipoxin by the transport system stimulates or inhibits a particular response. For example, a physiological response by a cell which is increased by uptake of a lipoxin by the lipoxin transport system can be increased by contacting the cell with an enhancer of the lipoxin transport system to increase lipoxin uptake by the cell. Alternatively, a physiological response which is decreased by uptake of a lipoxin by the lipoxin transport system can be decreased by contacting the cell with an enhancer of the lipoxin transport system to increase lipoxin uptake by the cell.

One type of physiological response which can be modulated by lipoxins is phagocytosis by neutrophils. $LXA_4$ and $LXB_4$ can inhibit phagocytosis by neutrophils which have been stimulated to be phagocytic (e.g., by exposure to particulate agents, such as red blood cells [see Example 9], microorganisms or crystals; while not required, the level of phagocytosis can be further enhanced by soluble stimuli such as FMLP). The inhibition of phagocytosis mediated by $LXA_4$ displays a pH dependence which is consistent with $LXA_4$ being taken up by the neutrophils by the lipoxin transport system. Accordingly, it is likely that neutrophil phagocytosis can be increased by decreasing lipoxin uptake by the lipoxin transport system (e.g., by raising the extracellular pH or by contacting the cell with an inhibitor of the lipoxin transport system). Alternatively, it is likely that neutrophil phagocytosis can be decreased by increasing lipoxin uptake by the lipoxin transport system (e.g., by lowering the extracellular pH or by contacting the cell with an enhancer of the lipoxin transport system).

Other neutrophil-mediated physiological responses may also be stimulated or inhibited by uptake of lipoxins by the lipoxin transport system. For example, it has been shown that $LXA_4$ can inhibit chemotaxis of polymorphonuclear leukocytes (Lee, T. H., et al. (1991) *Biochem. Biophys. Res. Commun.* 180:1416). Many neutrophil-mediated responses can be measured by standard in vitro assays. For example, neutrophil chemotaxis and granule enzyme release can be assayed as described in Simchowitz, L. and Cragoe, E. J. (1986) *J. Biol. Chem.* 261:6492–6500. The generation of superoxide radicals by neutrophils can be measured as described in Simchowitz, L. (1985) *J. Clin. Invest.* 76:1079–1089. These assays can be performed in the presence and absence of lipoxins (e.g., $LXA_4$ and/or $LXB_4$) to determine the effect of lipoxins (e.g., stimulation or inhibition) on these neutrophil responses. It can then be determined whether a physiological response by a neutrophil which is modulated (e.g., up- or down-regulated) by a lipoxin involves uptake of the lipoxin by the lipoxin transport system on the neutrophil. For example, the response can be measured in the presence of the lipoxin together with an inhibitor or enhancer of the lipoxin transport system (e.g., pH 8.4 can be used to inhibit the activity of the lipoxin transport system or an inhibitory compound can be used; alternatively, pH 6.4 can be used to enhance the activity of the lipoxin transport system or an enhancer compound can be used).

Additionally, many responses by other cell types (in addition to neutrophils) and many systemic responses are known to be stimulated or inhibited by lipoxins. For example, $LXA_4$ has vasodilatory effects and inhibits leukotriene-mediated vasoconstriction and leukotriene-mediated inflammation (see for example Badr, K. F. et al (1989) *Proc. Natl. Acad. Sci. USA* 86:3438; Hedqvist, P. et al. (1989) *Acta Physiol. Scand.* 137:571; Katoh, T. et al. (1992) *Am. J.Physiol.* 263 (Renal Fluid Electrolyte Physiol. 32) F436). $LXA_4$ can also stimulate myeloid bone marrow colony formation (see for example Stenke, L., et al. (1991) *Biochem. Biophys. Res. Commun.* 180:255). The involvement of the lipoxin transport system in uptake of lipoxins by cells, resulting in stimulation or inhibition of such responses, can be determined based upon the characteristics of the lipoxin transport system provided by the invention. Physiological responses in which lipoxin uptake is mediated by the lipoxin transport system can then be modulated using inhibitors, enhancers and inducers of the lipoxin transport system as described herein.

A lipoxin analog which maintains the ability to mediate physiological responses but which is transported at a faster rate than a natural lipoxin by a lipoxin transport system can also be used to modulate lipoxin-mediated responses. The invention provides a method for stimulating a lipoxin-mediated response by a cell which has a lipoxin transport system comprising contacting the cell with a lipoxin analog which is transported into the cell by the lipoxin transport system at a faster rate than a natural lipoxin. Such a lipoxin analog can be identified by procedures described earlier.

The present invention is further illustrated by the following examples which should in no way be construed as being further limiting. The contents of all references, issued patents and published patent applications cited throughout all portions of this application including the background are expressly incorporated by reference.

The following methodology was used in the Examples.

Incubation Media

The standard medium, Dulbecco's phosphate-buffered saline (PBS) with $Ca^{2+}$ and $Mg^{2+}$ (Bio-Whittaker

[Walkersville, Md.]), used in this study had the following composition: 138 mM NaCl, 8.1 mM $Na_2HPO_4$, 2.7 mM KCl, 1.1 mM $KH_2PO_4$, 0.9 mM $CaCl_2$, and 0.5 mM $MgCl_2$. The medium was supplemented with 5.6 mM glucose and the pH brought to 7.40 with NaOH. The cation composition of the media was manipulated by substituting equimolar amounts of either $K^+$ or N-methyl-D-glucamine for $Na^+$. For experiments in which the extracellular pH ($pH_o$) of the media was varied between 5.0 and 8.4, the solutions were buffered with MES (pK'6.0), HEPES (pK'7.3), or Tricine (pK'7.8) as appropriate.

Cell Isolation Procedures

Neutrophils: Human peripheral neutrophils were isolated from heparinized blood by sequential Ficoll-Hypaque (Pharmacia Fine Chemicals, Piscataway, N.J.) gradient centrifugation and dextran sedimentation at room temperature (Boyum, A. (1968) *Scand. J. Clin. Lab. Invest.* 21 (suppl. 97):77–89). Contaminating erythrocytes were removed by hypotonic lysis in 0.22% saline for 30 seconds. The neutrophils were washed twice and then counted. The purity of the neutrophil suspensions averaged 98%. Cell viability (>99%), as assessed by eosin Y exclusion, was not affected by any of the agents or incubation conditions tested. Cells were kept in the standard medium for 1 hour at 37° C. prior to experimentation. All assays were carried out at 37° C.

HL-60 Cells: HL-60 cells were seeded into RPMI medium supplemented with 100 U/ml penicillin, 100 μg/ml streptomycin, and 10% fetal calf serum (Hyclone, Logan, Utah) and grown at 37° C. in 250 ml flasks in a 5% $CO_2$/95% air atmosphere. Cells were induced to differentiate toward a neutrophil-like phenotype by exposure to 1 μM retinoic acid for 5 days.

Red Blood Cells (RBC): RBC were obtained directly from the heparinized blood of normal human donors. During repeated (four) washing steps, the uppermost portion of the cell pellets was aspirated and discarded to remove residual minor contamination of buffy coat cells.

Lymphocytes: The lymphocyte-rich interface layer was taken at the Ficoll-Hypaque gradient step of the neutrophil purification procedure. Platelets were removed by slow-speed centrifugation (see below) and contaminating monocytes and neutrophils by adherence to plastic Petri dishes for 1 hour at 37 ° C.

Platelets: Platelets were purified to homogeneity from acid citrate dextrose-treated blood according to established protocols (Romano, M. and Serhan, C. N. (1992) *Biochemistry* 31:8269–8277).

Radiolabeled Compounds

[11,12-$^3$H]LXA$_4$, henceforth designated [$^3$H]LXA$_4$, and its methyl ester derivative, [$^3$H]LXA$_4$ME, were prepared from 11,12-acetylenic LXA$_4$ME (Cascade) by a custom tritiation performed at the New England Nuclear/Dupont Tritiation Laboratory (Boston, Mass.).

The products were isolated by RP-HPLC as reported previously (Fiore, S. et al., (1992) *J. Biol. Chem.* 267:16168–16176) after LiOH saponification. The specific activity was 40.5 Ci/mmole.

Reagents and Chemicals

Inorganic salts were obtained from Fisher Scientific, St. Louis, Mo. The following reagents were purchased from Sigma Chemical Company, St. Louis, Mo.: N-methyl-D-glucamine, 4-(2-hydroxyethyl)-1-piperazineethanesulfonic acid (HEPES), 2-(N-morpholino)ethanesulfonic acid (MES), N-tris(hydroxymethyl)methylglycine (Tricine), Nethylmaleimide (NEM), D-glucose, 3,5-diiodosalicylic acid (DISA), mersalyl, pentachlorophenol (PCP), probenecid, sodium p-hydroxymercuribenzoate (pHMB), niflumic acid, and iodoacetic acid. 4-Acetamido-4'-isothiocyanostilbene-2,2'-disulfonic acid (SITS) was bought from Pierce Chemical Co., Rockford, Ill.; diphenylamine-2-carboxylic acid from Fluka; and arachidonic acid, prostaglandin $E_2$ (PGE$_2$), leukotriene B$_4$ (LTB$_4$), leukotriene C$_4$ (LTC$_4$), leukotriene D$_4$ (LTD$_4$), and 15-HETE from BIOMOL Research Laboratories, Plymouth Meeting, Pa. α-Cyano-β-(1-phenylindol-3-yl)acrylic acid (UK-5099) was graciously provided by Pfizer Central Research Laboratories, Sandwich, Kent, UK.

Unidirectional Tracer Flux Measurements

Incubations were performed at 37° C. in capped, plastic tubes (Falcon Plastics, Oxnard, Calif.) under various experimental conditions (neutrophils 15–20×10$^6$/ml). Influx experiments were performed in the presence of [$^3$H]LXA$_4$ or [$^3$H]LXA$_4$ME (0.1 μCi/ml) at a final concentration of 5 nM. At stated intervals, duplicate aliquots of the cell suspensions were layered onto 0.5 ml of silicone oil (Versilube F-5, General Electric Corp., Waterford, N.Y.) contained in 1.5 ml plastic tubes and centrifuged for 1 min at 8,000 g in a microcentrifuge (Beckman Instruments, Fullerton, Calif.). Cell separation occurred in <5 s.

The aqueous and oil phases were aspirated and discarded. The neutrophil pellets were excised and counted in a liquid scintillation counter (Wallac 1409, Pharmacia LKB Nuclear, Gaithersburg, Md.). Influx is expressed here as fmol/10$^6$ cells/min whereas flux rates in all previous work from our laboratory (L.S.) have been reported in meq/liter of cell water.min.

For ease of comparison, the unit of fmol/10$^6$ cells/min can be converted to nmol/liter of cell water.min by dividing by 0.274 based on a cell water volume of 0.274 μl/10$^6$ cells (Simchowitz, L., et al. (1992) *J. Gen. Physiol.* 22:453–479). For efflux studies, neutrophils were loaded with [$^3$H]LXA$_4$ (0.1 μCi/ml) for 15 min at 37° C. in the standard medium.

Thereafter, the cells were spun down and then resuspended in the various experimental solutions at 37° C. Aliquots were taken at stated intervals for measurement of the amount of residual radioactivity that remained associated with the cell pellet. Samples were spun over silicone oil and handled as described for influx studies.

Ligand Binding Assays

Binding experiments were performed at 4° C. in an ice-water bath as described above for the tracer flux determinations except that the fmal concentration of [$^3$H]LXA$_4$ was reduced to 0.3 nM. This value approximates the K$_d$ for binding (0.5±0.3 nM, Fiore (1992) *J. Biol. Chem.* 267:16168–16176). Unlabeled LXA$_4$ was added to a parallel set of tubes in 1000-fold excess to determine total and nonspecific binding, respectively.

Data Analysis

Transport system-mediated influx of [$^3$H]LXA$_4$, corrected for the very rapid (complete within 1 min), inhibitor-resistant specific binding, followed equations of the form:

$$C_t = C_\infty[1 = \exp(-kt)] \quad (1)$$

where $C_t$ is the cell label at time t, $C_\infty$ is the cell label at steady-state, and k is the rate coefficient. Equation 1 was fit to the data by a nonlinear least-squares program, and the initial influx rate computed from the product $kC_\infty$. The change in some of the measured variables often appeared to be linear over the period of study; in those cases, the influx rate was computed from the slope of the linear regression line. Trapping of label within the extracellular space of the cell pellet, determined using [$^3$H]H$_2$O and [$^{14}$C]inulin, was negligibly small. The efflux rate coefficients were computed by least-squares fitting the time course data to a single exponential equation.

Abbreviations

The abbreviations used are: lipoxin $A_4$ (LXA$_4$), (5S,6R,15S)-trihydroxy-7,9,13-trans-11-cis-eicosatetraenoic acid; lipoxin $A_4$ methyl ester (LXA$_4$ME); 3,5-diiodo-salicylic acid (DISA);

pentachlorophenol (PCP); α-cyano-β-(1-phenylindol-3-yl)acrylic acid (UK-5099); p-hydroxymercuribenzoate (pHMB); N-ethylmaleimide (NEM); 4-acetamido-4'-isothiocyanostilbene-2,2'-disulfonic acid (SITS); prostaglandin $E_2$ (PGE$_2$); leukotriene $B_4$ (LTB$_4$), (5S,12R)-dihydroxy-6,14-cis-8,10-trans-eicosatetraenoic acid; leukotriene $C_4$ (LTC$_4$), (5S)-hydroxy-(6R)-S-glutathionyl-7,9-trans-11,14-cis-eicosatetraenoic acid; leukotriene $D_4$ (LTD$_4$), (5S)-hydroxy-(6R)-S-cysteinylglycyl-7,9-trans-11,14-ciseicosatetraenoic acid; 15-HETE, (15S)-hydroxy-5,8,11-cis-13-trans-eicosatetraenoic acid; reverse phase-high pressure liquid chromatography (RP-HPLC).

EXAMPLE 1

Effect of Inhibitors and pH on LXA$_4$ Influx into Neutrophils

The time course of influx of [$^3$H]LXA$_4$ into isolated human neutrophils is presented in FIG. 1. Also shown is the effect, or lack thereof, of different extracellular ionic conditions and drugs. At zero-time, cells were resuspended in media containing labeled LXA$_4$ at a total concentration of 5 nM. At stated times, aliquots of the neutrophil suspensions were taken and the cell pellets isolated by rapid centrifugation through a cushion of silicone oil and counted for radioactivity. Cell-associated [$^3$H]LXA$_4$ is expressed as fmol/$10^6$ cells. Results represent the means±SEM of three to seven separate experiments, each performed in duplicate.

The studies shown in the left panel were conducted in the presence of medium alone at pH$_o$ 7.40 (Control), 1 mM probenecid, 0.4 mM SITS, Na$^+$-free medium (equimolar replacement by N-methyl-D-glucamine), high K$^+$ medium (120 mM K$^+$, 25 mM Na$^+$), medium at pH$_o$ 6.40, and medium at 8.40. The upper and middle curves are single exponential fits of the data points starting at 2.88 fmol/$10^6$ cells: for pH$_o$ 6.40 (upper curve), initial influx rate=5.5±1.0 fmol/$10^6$ cells/min and fmal uptake=15.1±0.6 fmol/$110^6$ cells; for Control, SITS, probenecid, Na$^+$-free medium, and high K$^+$ medium (combined data, middle curve), initial influx rate=0.57±0.09 fmol/$10^6$ cells/min and final uptake=7.26±0.26 fmol/$10^6$ cells. The pH$_o$ 8.40 data were fit to a straight line with a slope=–0.002±0.013 fmol/$10^6$ cells/min.

The studies shown in the right panel were conducted in the presence of medium alone, 0.5 mM DISA, 0.5 mM mersalyl, 0.4 mM PCP, and 0.2 mM UK-5099. The Control data set is the same as that shown in the left-hand panel. Note, however, that the Y-axis scale is different in the two panels. The curves for medium (Control), mersalyl, UK-5099, and PCP are single exponential fits with initial influx rates of 0.57±0.12, 0.10±0.01, 0.030±0.009, and 0.015±0.004 fmol/$10^6$ cells/min. A horizontal line has been drawn at 2.88, the average of all of the DISA data points (a fit of the DISA data set to a straight line gave a slope of 0.0046±0.0051 fmol/$10^6$ cells/min, which could not be distinguished from zero).

From an external concentration of 5 nM, uptake under control conditions appears to be divisible into at least two components: (1) a rapid portion that is complete by 1 min, equivalent to ~3 fmol/$10^6$ cells and (2) a more gradual and prolonged phase that takes place over the next 30 min. This impression was confirmed through the use of a variety of different inhibitors and extracellular pH. Inspection of data in the left and right panels reveals that DISA, PCP, UK-5099, and mersalyl (each at 0.2–0.5 mM) all inhibited the uptake of [$^3$H]LXA$_4$. These compounds have previously been observed to block several different anion transport processes in human neutrophils including Cl$^-$/HCO$_3^-$-exchange (Simchowitz, L., et al. (1988) in *Cell Physiology of Blood* (Gunn, R. B. and Parker, J. C., eds.) pp. 193–208, Rockefeller University Press, New York; Simchowitz, L., et al. (1991) *Am. J. Physiol.* 261:C906–C915), H$^+$+lactate$^-$ cotransport (Simchowitz, L. and Textor, J. A. (1992) *J. Gen. Physiol.* 100:341–367), and cell swelling-induced Cl$^-$ channels (Stoddard, J. S., et al., (1993) *Am. J. Physiol.* 26:C156–C165). Of interest, two general inhibitors of anion transport in these and other cells (Simchowitz, L. and Davis, A. O. (1989) *J. Gen. Physiol.* 94:95–124), probenecid (1 mM) and the disulfonic stilbene SITS (0.4 mM), had no apparent impact on [$^3$H]LXA$_4$ influx. All of these drugs are weak organic acids (pK'4-6) so that at physiologic pH they exist predominantly in the form of anions. This should also be the case for LXA$_4$ and on this basis, we speculated that at least one of the two components of [$^3$H]LXA$_4$ uptake might represent a specialized transport system for LXA$_4$ anion. The analysis to follow demonstrates that the initial, rapid portion of LXA$_4$ uptake can be largely ascribed to specific binding to putative receptors while the second, more gradual phase of uptake indeed represents transport system-mediated influx into the cell.

In the presence of 0.5 mM DISA, 2.9 fmol/$10^6$ cells of uptake occurs by 1 min of incubation, but no additional increase in cell-associated counts can be detected over the next 30 min. We propose that the uptake observed at 1 min constitutes binding to receptors and that this concentration of DISA completely blocks the second component of uptake referable to transport system-mediated transport. Note that the second phase of [$^3$H]LXA$_4$ influx with all of the other drugs also appears to originate at the same starting value, namely, ~3 fmol/$10^6$ cells at 1 min. If this indeed represents receptor binding, this level signifies ~1700 sites/cell which agrees with the finding of ~1830 sites/cell previously reported (Fiore, S., et al., (1992) *J. Biol. Chem.* 26:16168–16176).

Considering the DISA-resistant uptake as background, influx into control cells proceeded at a rate of 0.57±0.12 fmol/$10^6$ cells/min. In the presence of 0.4 mM PCP, 0.2 mM UK-5099, and 0.5 mM mersalyl, influx rates of 0.015±0.004, 0.030±0.009, and 0.10± 0.01 fmol/$10^6$ cells/min were observed, corresponding to inhibitions of 97, 95, and 82%.

Marked inhibition (>85%) was also observed with 0.5 mM diphenylamine-2-carboxylate and 0.2 mM niflumate. Reverse phase-high pressure liquid chromatography analysis using tandem electrochemical detection and ultraviolet monitoring indicated preservation of the integrity of LXA$_4$ after 30 min of exposure to DISA, PCP, UK-5099, and mersalyl. These findings indicate that lack of appreciable uptake of [$^3$H]LXA$_4$ in the presence of inhibitors was not the result of either chemical degradation or the interaction of [$^3$H]LXA$_4$ with the drugs.

EXAMPLE 2

The LXA$_4$ Transport System Is Consistent With an Anion Cotransport System

The possible ionic basis of this presumed DISA-inhibitable LXA$_4$ transport was investigated next. The data of FIG. 1 (left panel) indicate that complete removal of extracellular Na$^+$ (equimolar replacement by N-methyl-D-glucamine$^+$) had no significant effect on total uptake, thereby negating a Na$^+$-dependent process. Likewise, raising extracellular K$^+$ from 4 to 120 mM, thereby depolarizing membrane voltage from ~−60 to ~0 mV, caused no change in the time course of [$^3$H]LXA$_4$ entry. This finding lends credence to an electroneutral mechanism. In contrast, varying extracellular pH had a profound effect: lowering pH$_o$ to 6.40 dramatically increased both the initial rate and the final steady-state level of uptake, while raising pH$_o$ to 8.40 essentially abolished uptake, reducing influx to levels indistinguishable from that with DISA. In fact, at pH$_o$ 8.40, there was no measurable DISA-sensitive influx. The enhancement of [$^3$H]LXA$_4$ influx by acidification and suppression by alkalinization are compatible with an H$^+$+LXA$_4$ anion cotransport system. These results, however, are equally consistent with (a) entry of LXA$_4$ by non-ionic diffusion as the undissociated free acid, (b) pH-induced changes in binding to or recruitment of surface receptors, and (c) allosteric effects of pH on the hypothetical transporter.

EXAMPLE 3

LXA$_4$ Transport Is Not By Ionic Diffusion or by Specific Receptor Binding

Figure 2:
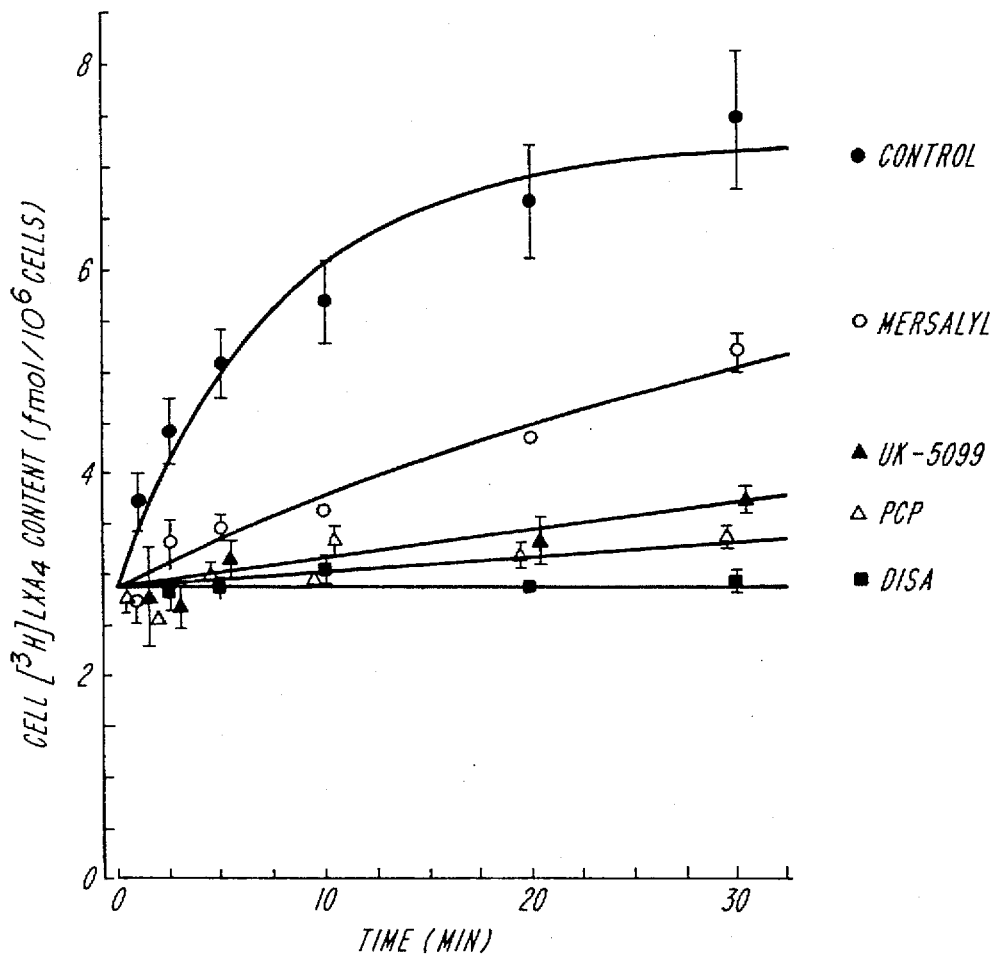
FIG. 2 is a graph depicting the time couse of [$^3$H]$LXA_4$ influx into neutrophils in the presence of medium alone, DISA, mersalyl, PCP and UK-5099.

Three lines of evidence provide strong arguments against an appreciable role for simple diffusion of LXA$_4$ as the free acid. First, the pH dependence of [$^3$H]LXA$_4$ influx into neutrophils was measured (FIG. 2). The studies were conducted as in FIG. 1 in media wherein the pH$_o$ was varied between 5.0 and 8.3. The uptake of [$^3$H]LXA$_4$ was determined at three different time points that were relevant to the wide range of influx rates observed (e.g., 0.25, 0.5, and 0.75 min in the case of pH$_o$ 5.0–6.5; 1, 2.5, and 5 min for pH$_o$ 6.8–7.1; and 5, 10, and 20 min for pH$_o$ 7.4–8.3). Influx rates were calculated after subtraction of the DISA-resistant, carrier-independent component that most likely represents binding to receptors.

The data points have been fit to a titration curve which yielded a pK' of 5.9±0.1. Results have been taken from four experiments. The data of FIG. 2, which displays the rate of LXA$_4$ influx as a function of pH$_o$, yields an apparent pK of 5.9±0.1. This value is about 2 pH units more alkaline than the pK' (~3.8) of the carboxylic acid moiety of LXA$_4$. If entry were predominantly through non-ionic diffusion then an effective pK of ~4 would be expected. Second, one would not anticipate an LXA$_4$ influx pathway such as non-ionic diffusion to exhibit the striking sensitivity to DISA, PCP, UK-5099, and mersalyl. The final piece of supporting evidence for the mechanism underlying LXA$_4$ influx being other than that of non-ionic diffusion is shown in Table I. Here, the effect of various drugs on the uptake of [$^3$H]LXA$_4$ methyl ester was measured. This compound is uncharged by virtue of the ester linkage through the carboxyl group and is very lipophilic. As such, LXA$_4$ME should permeate via simple diffusion, a process one would predict to be very rapid and not sensitive to the drugs which block influx of LXA$_4$ free acid. All of these expectations were verified by the data of Table I. [$^3$H]LXA$_4$ME influx rates in medium alone averaged 535±136 fmol/10$^6$ cells/min, 1,000-fold faster than for LXA$_4$ free acid and were completely resistant to concentrations of DISA, PCP, and mersalyl which inhibit [$^3$H]LXA$_4$ influx by >80%. Moreover, given the lack of a titratable carboxylic acid group, LXA$_4$ME uptake did not display the marked pH-dependence characteristic of LXA$_4$ influx.

TABLE I

[$^3$H]LXA$_4$ Methyl Ester Influx and [$^3$H]LXA$_4$ Binding to Human Neutrophils: Lack of Effect of Drugs and Extracellular pH

| Conditions | [$^3$H]LXA$_4$ME Influx (fmol/10$^6$ cells/min) | Unlabeled LXA$_4$ 0.3 µM | [$^3$H]LXA$_4$ Binding (fmol/10$^6$ cells) |
|---|---|---|---|
| Medium | 535 ± 136 | − | 1.05 ± 0.03 |
| Medium |  | + | 0.40 ± 0.08 |
| DISA 0.5 mM | 481 ± 170 | − | 1.23 ± 0.08 |
| DISA 0.5 mM |  | + | 0.41 ± 0.05 |
| PCP 0.4 mM | 439 ± 63 | − | 1.18 ± 0.04 |
| PCP 0.4 mM |  | + | 0.36 ± 0.04 |
| Mersalyl 0.5 mM | 500 ± 184 | − | 1.13 ± 0.05 |
| Mersalyl 0.5 mM |  | + | 0.39 ± 0.03 |
| pH$_o$ 6.40 | 465 ± 45 | − | 1.02 ± 0.09 |
| pH$_o$ 6.40 |  | + | 0.39 ± 0.04 |
| pH$_o$ 8.40 | 553 ± 129 | − | 1.19 ± 0.12 |
| pH$_o$ 8.40 |  | + | 0.42 ± 0.09 |

Neutrophils were resuspended in the various media containing [$^3$H]LXA$_4$ME at a concentration of 5 nM. Uptake was measured at 37° C. as in FIG. 1 though at 15 s intervals through 1 min due to the very rapid kinetics. Influx rates were calculated by fitting the data points to a single exponential equation (Eq. 1). Results have been taken from three experiments based upon duplicate determinations. The binding of [$^3$H]LXA$_4$ to human neutrophils was assessed at 4° C. at a final concentration of 0.3 nM. Cells were exposed to the drugs and different pH$_o$ media simultaneously along with LXA$_4$. Total binding was determined after 5 min of incubation and is given on the line denoted by the "−" sign under the heading "unlabeled LXA$_4$ 0.3 µM". Non-specific binding was measured, also at 5 min, in the presence of a 1,000-fold excess of unlabeled LXA$_4$ (0.3 µM) and is given on the line where the "+" sign appears. Specific binding was taken as the difference between total and non-specific binding. There were no significant differences in any of these parameters under any of the treatment conditions. Results are from three separate experiments, each performed in triplicate.

Recently, binding of [$^3$H]LXA$_4$ to specific binding sites has been demonstrated and specific binding has been correlated with functional responses in both neutrophils and HL-60 cells (Fiore, S., et al. (1992) *J. Biol. Chem.* 27:16168–16176; Fiore, S., et al. (1993) *Blood* 81:3395–3403). Specific binding, defined as the cell-associated label which could be displaced in the presence of a 1,000-fold excess of unlabeled LXA$_4$, amounted to ~70% of total binding (Table I) and was observed at both 4° C. and 37° C. Further investigations at 4° C. indicated a K$_d$ of 0.5±0.3 nM with ~1830 binding sites/cell and a half-time for binding of . 15 s. Conceivably, changes in receptor binding at 37° C. as compared to 4° C. where most of the previous studies were conducted, could account for the progressive increase in cell-associated LXA$_4$ counts between 1 and 30 min (FIG. 1). Up-regulation, recycling, or recruitment of new receptors and changes in affinity are only a few of the many possible examples. As given in Table I, however, none of the experimental maneuvers, including drugs (DISA, PCP, and mersalyl) or varying pH$_o$ (6.4–8.4) had any significant effect on specific (or non-specific) association of [$^3$H]LXA$_4$ with its surface receptors. These findings indicate that specific binding to cell surface receptors cannot account for the present results.

The above mentioned results essentially rule out non-ionic diffusion and receptor binding as likely possibilities to explain the second phase of $LXA_4$ influx. This process is in all likelihood due to a carrier-mediated $H^+$+LXA4-cotransport system or some other formal equivalent such as $LXA_4^-/OH^-$ (or $HCO_3^-$) exchange.

EXAMPLE 4

Inhibitor Profile of the $LXA_4$ Transport System

Figure 3:
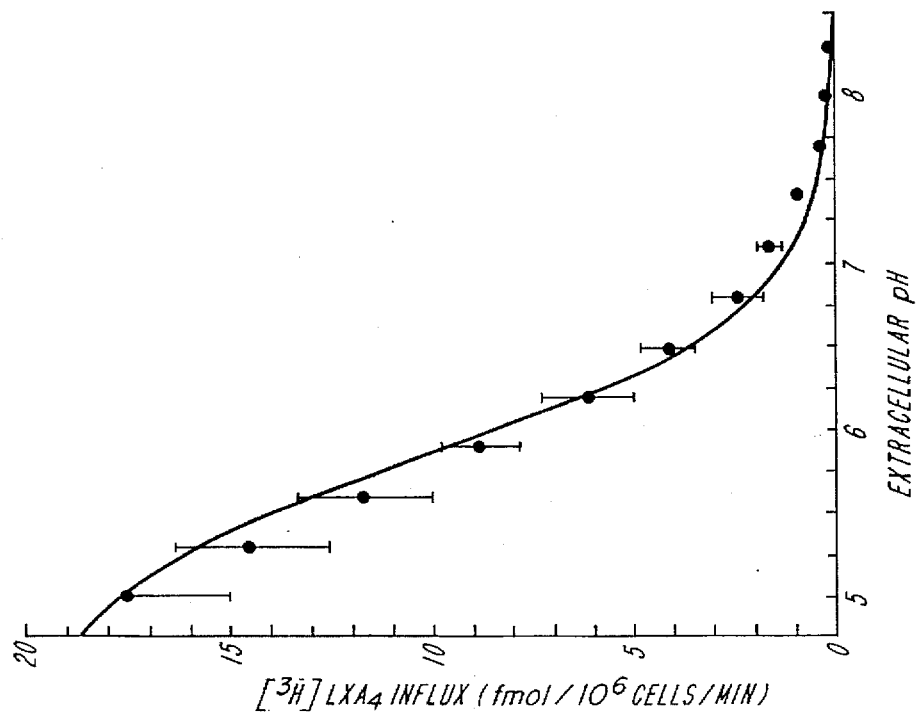
FIG. 3 is a graph depicting the pH-dependence of [$^3$H] $LXA_4$ influx into neutrophils, wherein the $pH_o$ of the media was varied between 5.0 and 8.3.

The dose-dependencies of inhibition of $LXA_4$ influx by DISA, PCP, and mersalyl are depicted in FIG. 3. Studies were performed as in FIG. 1 in the presence of varying concentrations of DISA, PCP, and mersalyl (0–500 uM). Uptake was measured at 10 and 20 min and the data points fit to single exponentials as described in the legend to FIG. 1. Transport influx rates were determined after subtraction of non-transport system-mediated uptake, the latter taken as that occurring at $pH_o$ 8.40 or in the presence of 1 mM DISA. The initial influx rates have been plotted against the added drug concentration. Results have been taken from three experiments for each condition.

In these studies, the receptor-bound component, taken as non-transport system-mediated uptake, was determined by performing studies at $pH_o$ 8.4 or in the presence of 1000 µM DISA. This "transport system-independent background" was then subtracted from the total uptake at any given time interval in order to derive the transport system-mediated influx. The data sets for the three drugs followed simple Michaelis-Menten inhibition kinetics, the curves yielding $K_{0.5}$ values of 12±2 µM for DISA, 25±5 µM for PCP, and 112±33 µM for mersalyl. As remarked above, all of these agents behave as anions which presumably compete, although this remains to be proven conclusively, with $LXA_4^-$ for binding to the external translocation site of the $LXA_4^-$ carrier.

In addition to its being an anion, mersalyl, an organomercurial, is also a sulfhydryl-reactive agent, suggesting the possibility that a critical thiol group on the transport protein may be implicated. In view of this, a few other SH-reactive compounds were evaluated for activity. However, 1 mM NEM and 0.4 mM iodoacetate lacked efficacy in this system. Guided by prior experience in our identification of a mersalyl-sensitive $H^+$+lactateco-transport system in these cells (Simchowitz, L. and Textor, J. A. (1992) J. Gen Physiol 100:341–367; Simchowitz, L. and Vogt, S. K. (1993) J. Membr. Biol. 131:23–34), we examined the question of whether any of a number of SH-reactive compounds might cause irreversible inhibition of $[^3H]LXA_4$ influx when preincubated with neutrophils. For these studies (Table II), cells were pretreated with drugs for 30 min at 4° C. in order to prevent metabolic production of lactic acid and its intracellular accumulation and resultant fall in intracellular pH consequent to a block of the lactate carrier (Simchowitz, L. and Textor, J. A. (1992) J. Gen Physiol 100:341–367). As shown, 0.25 mM mersalyl and pHMB, a related organomercurial, led to ~65% irreversible inhibition when cells were subsequently washed and assayed for their ability to transport $[^3H]LXA_4$ at 37° C. NBD-CL and eosin-5-maleimide caused more modest inhibition (~20%) while 2,2'-DTBP was without appreciable effect.

TABLE II

Ability of Sulfhydryl-Reactive Agents to Cause Irreversible Inhibition of $[^3H]LXA_4$ Influx

| Compound | Concentration (mM) | % Inhibition of Transport |
|---|---|---|
| Mersalyl | 0.25 | 67 ± 5 |
| pHMB | 0.25 | 66 ± 4 |
| NBD-Cl | 0.25 | 22 ± 7 |
| 2,2'-DTBP | 0.50 | 5 ± 3 |
| Eosin-5-maleimide | 0.50 | 19 ± 6 |

Aliquots of a neutrophil suspension were pretreated with drugs at the stated concentrations for 30 min at 4° C. Thereafter, the cells were washed once to get rid of excess free drug and finally resuspended in medium containing $[^3H]LXA_4$ at 5 rM. Uptake was measured at 1, 5, and 10 min and the initial influx rates determined as detailed in the legends to FIGS. 1 and 2. Influx rates after preincubation with the various thiol reagents were compared to those with medium alone (0% inhibition) and with 0.5 mM DISA (taken as 100% inhibition) in order to calculate the % inhibition of transport system-mediated transport. Results represent the means+SEM of three separate experiments for each condition. NBD-Cl=7-chloro-4-nitrobenz-2-oxa-1,3-diazole; 2,2'-DTBP=2,2'-dithiobispyridine.

EXAMPLE 5

Enhancers of $LXA_4$ Transport by the Transport System

Figure 4:
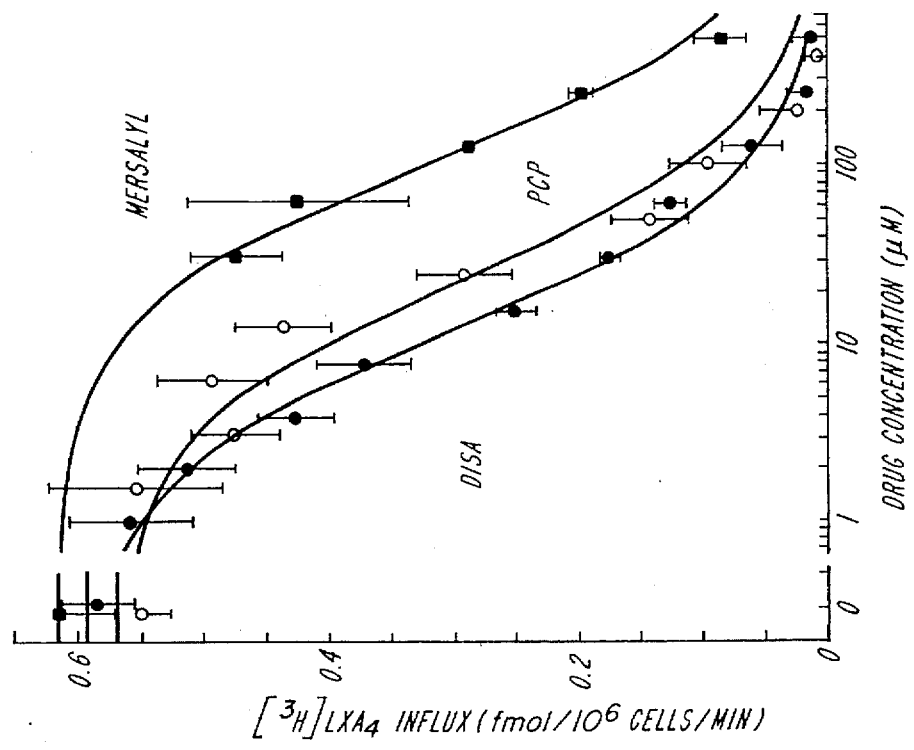
FIG. 4 is a graph depicting the dose-dependencies of transport inhibitors with respect to inhibition of [$^3$H]$LXA_4$ influx into neutrophils, wherein the concentrations of DISA, PCP and mersalys were varied between 0–500 μM.

Certain compounds were found to enhance rather than inhibit uptake of $LXA_4$ by neutrophils via the lipoxin transport system. $[^3H]LXA_4$ influx experiments were performed as described in the previous examples in the presence or absence of 100 nM n-formylmethionyl-leucyl-phenylalanine (FMLP) or phorbol myristate acetate (PMA), a phorbol diester. Exposure of neutrophils to 100 nM FMLP led to a ~2-fold increase in the initial rate of $[^3H]LXA_4$ influx, as shown in FIG. 4. The enhanced uptake was completely sensitive to inhibition by DISA, characteristic of uptake by the lipoxin transport system. Exposure of neutrophils to 100 nM PMA caused a ~4-fold increase in the initial rate of $[^3H]LXA_4$ entry into cells (see FIG. 4). (The apparent decrease in uptake seen after 10 minutes most likely represents degradation of the radiolabeled probe). In contrast, 4-α-PMA, a biologically inactive isomer of PMA, had no effect on lipoxin uptake, thereby ruling out non-specific detergent-like actions of PMA on the neutrophil membrane. The PMA-induced enhancement of $[^3H]LXA_4$ influx was likewise competely sensitive to inhibition by DISA. The divalent cation ionophore A23187 (at 1 µM concentration) also had a modest stimulatory effect (~1.5-fold enhancement) on lipoxin uptake.

EXAMPLE 6

Additional Properties of the $LXA_4$ Transport System

Substrate Saturation

Figure 5:
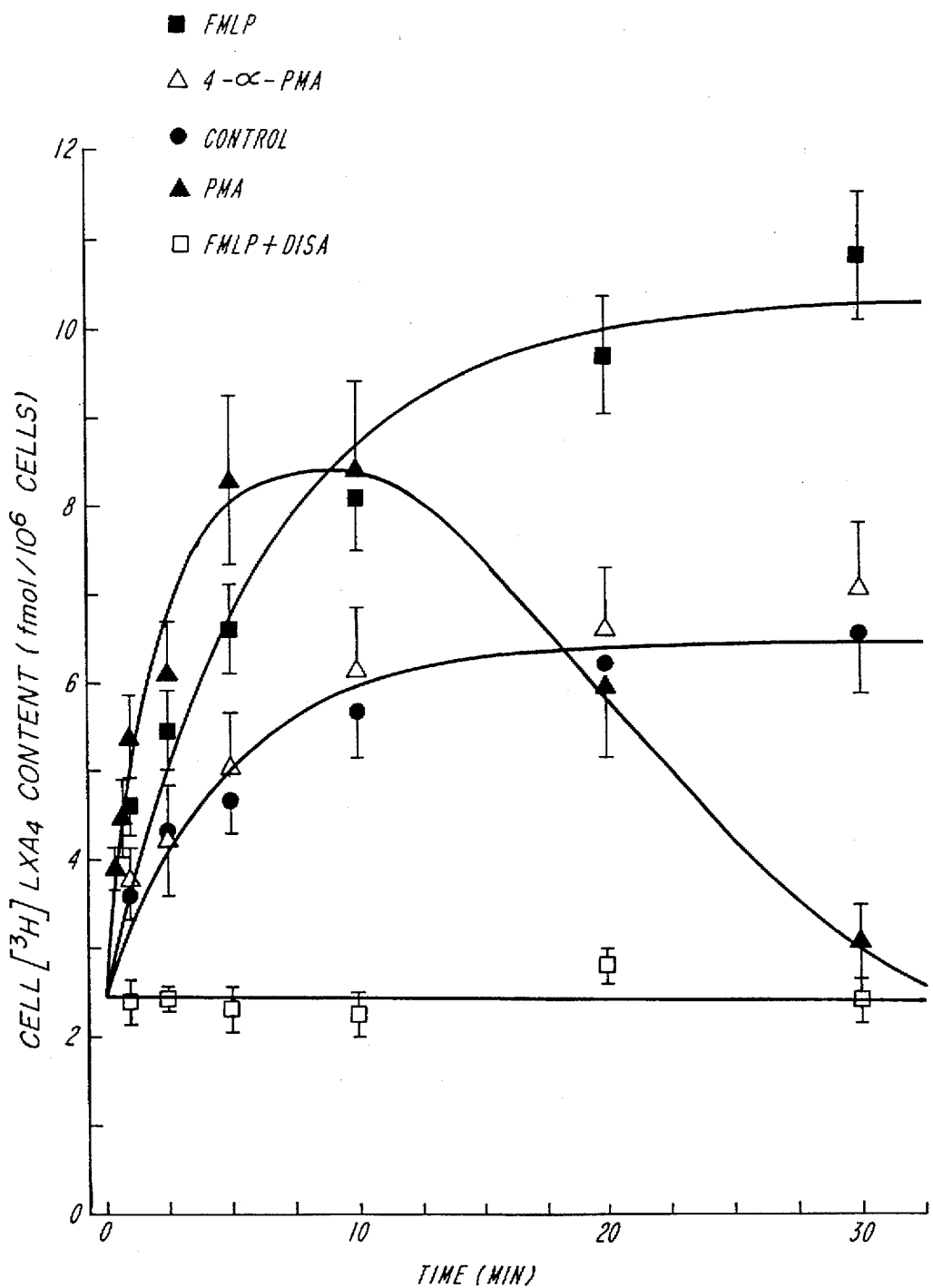
FIG. 5 is a graph depicting the time couse of [$^3$H]$LXA_4$ influx into neutrophils in the presence of medium alone, FMLP, PMA, 4-α-PMA or FMLP+DISA.

Carrier-mediated $LXA_4$ transport would be expected to display the general property of substrate saturation and so we monitored the rate of $[^3H]LXA_4$ influx as a function of added $LXA_4$ concentration between 0.6 nM and 5 µM (FIG. 5). Experiments were carried out as in FIG. 1 in the presence of a constant amount of $[^3H]LXA_4$. Increasing quantities of unlabeled $LXA_4$ were added to achieve total concentrations of 0.6 nM to 5 µM. Uptake was measured at 5 and 10 min and the influx rates calculated as described for FIG. 2. As shown, a linear relationship applies when the $[^3H]MLXA_4$ influx rates are plotted against the $LXA_4$ concentration: slope=0.116±0.003. Results are from three experiments. Contrary to expectation, over a 4 log dose range, no tendency towards saturation was evident and influx remained strictly proportional to the $LXA_4$ concentration. It is important to point out that in these experiments $[^3H]LXA_4$ uptake was always markedly sensitive to 0.5 mM DISA. As 5 µM $LXA_4$ approaches or exceeds the upper limit of the physiologically relevant range, higher concentrations were not tested.

Temperature-Dependence

Figure 6:
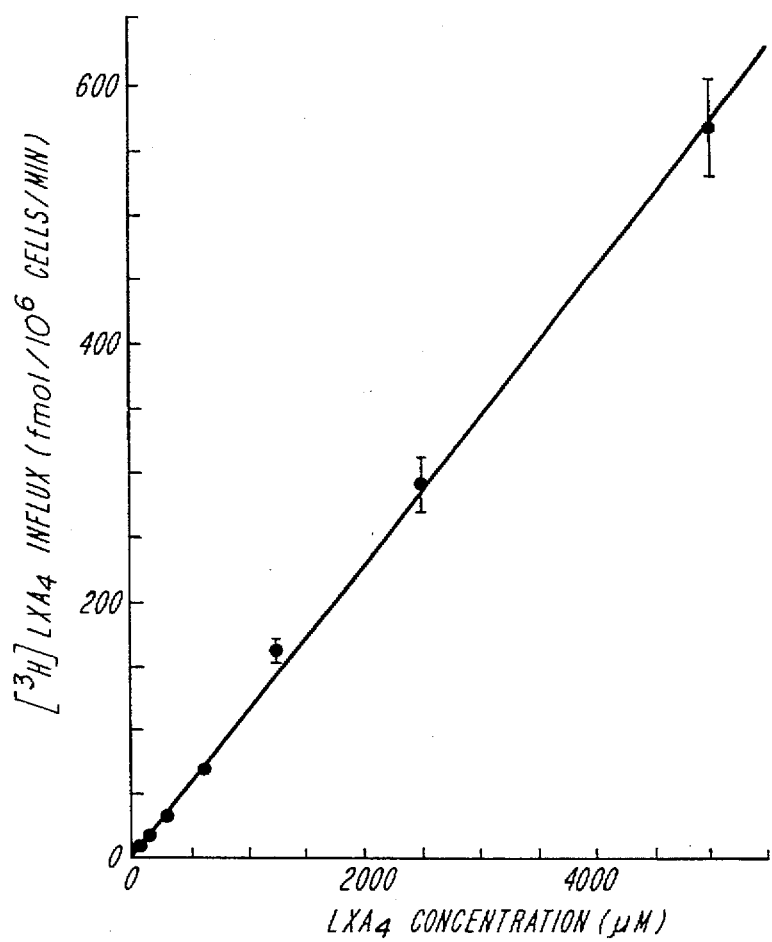
FIG. 6 is a graph depicting the relationship between [$^3$H]$LXA_4$ influx rate and $LXA_4$ concentration demonstrating lack of substrate saturation. Increasing quantities of unlabeled $LXA_4$ were added to a constant amount of [$^3$H] $LXA_4$ to achieve total concentrations of 0.6 nM to 5 μM.

To assess the temperature-dependence of the transport reaction, we also determined the rate of DISA-sensitive $[^3H]LXA_4$ influx as a function of temperature between 4° and 37° C. Uptake of $[^3H]LXA_4$ was measured at three different points along the entire time course (1–30 min) and influx rates were determined as for FIG. 2. Results are from three experiments. The data are graphed in FIG. 6 in the form of a conventional Arrhenius plot. The results convey a linear relationship exhibiting a rather shallow slope that translates into a relatively low activation energy of 15.0±0.8 cal/mole.

Effect of Different Eicosanoids

The effect of a number of other eicosanoids on the influx rate of $[^3H]LXA_4$ was also evaluated (Table III). The studies were based on the rationale that these agents might behave as competing substrates and therefore reduce $LXA_4$ transport were they to share the same carrier and bind with high affinity. The data reveal, however, that over the concentration range 10–100 nM, neither arachidonic acid, $PGE_2$, 15-HETE, $LTB_4$, nor the cysteinyl leukotrienes $LTC_4$ and $LTD_4$ perturbed the rate of $[^3H]LXA_4$ uptake. These results provide evidence that the $LXA_4$ carrier system is distinct and probably does not represent a common, more generalized transport pathway for a wide variety of arachidonate-derived products.

TABLE III

Lack of Effect of a Variety of Eicosanoids on $[^3H]LXA_4$ Influx into Neutrophils

| Conditions | Concentration (nM) | $[^3H]LXA_4$ Influx (fmol/$10^6$ cells/min) |
|---|---|---|
| Control |  | 0.66 ± 0.04 |
| Arachidonic Acid | 100 | 0.70 ± 0.02 |
| Arachidonic Acid | 30 | 0.66 ± 0.02 |
| Arachidonic Acid | 10 | 0.69 ± 0.03 |
| $PGE_2$ | 100 | 0.60 ± 0.03 |
| $PGE_2$ | 30 | 0.59 ± 0.03 |
| $PGE_2$ | 10 | 0.58 ± 0.03 |
| 15-HETE | 100 | 0.71 ± 0.06 |
| 15-HETE | 30 | 0.69 ± 0.05 |
| 15-HETE | 10 | 0.73 ± 0.05 |
| $LTB_4$ | 100 | 0.70 ± 0.06 |
| $LTB_4$ | 30 | 0.64 ± 0.04 |
| $LTB_4$ | 10 | 0.67 ± 0.04 |
| $LTC_4$ | 100 | 0.78 ± 0.07 |
| $LTC_4$ | 30 | 0.76 ± 0.05 |
| $LTC_4$ | 10 | 0.70 ± 0.05 |
| $LTD_4$ | 100 | 0.61 ± 0.03 |
| $LTD_4$ | 30 | 0.59 ± 0.04 |
| $LTD_4$ | 10 | 0.63 ± 0.03 |

Experiments were performed as described for FIG. 3 in the presence of stated concentrations of eicosanoids. The neutrophils were exposed to the compounds at zero-time and uptake of $[^3H1]LXA_4$ was assessed at 10 and 20 min. Results are from three experiments for each condition.

EXAMPLE 7

Presence of the $LXA_4$ Transport System in Other Blood Cells

It was next determined whether or not a similar lipoxin transport activity might be present in other blood cells (Table IV). For these studies, purified suspensions of unstimulated human erythrocytes, lymphocytes, and platelets that were isolated from peripheral blood were used as well as undifferentiated HL-60 cells, a stable human promyelocytic leukemia cell line, and retinoic acid-induced HL-60 cells which display many of the phenotypic features of normal mature neutrophils (Collins, S., et al., (1978) *Proc. Natl. Acad. Sci. USA* 75:2458–2462). As shown in Table IV, there was no DISA-sensitive component of $[^3H]LXA_4$ uptake into unstimulated human red cells, lymphocytes, platelets, or undifferentiated HL-60 cells. The results imply that these cell types in a resting state do not express an $LXA_4$ carrier on their plasma membranes. In contrast, HL-60 cells that had been terminally differentiated along a neutrophil-like pathway by a 5-day exposure to 1 µM retinoic acid acquired a new DISA-sensitive influx route for $LXA_4$ that strongly resembled that of normal neutrophils in time course and magnitude.

TABLE IV

Presence of an $LXA_4$ Transport System in Other Blood Cells

| | $[^3H]LXA_4$ Uptake Rates (fmol/$10^6$ cells/min) in the presence of: | |
|---|---|---|
| Cell Type | Medium | DISA |
| Erythrocytes | 0.0014 ± 0.0006 | 0.0019 ± 0.0008 |
| Lymphocytes | 0.0019 ± 0.0048 | 0.0053 ± 0.0036 |
| Platelets | −0.0003 ± 0.0015 | −0.0005 ± 0.0015 |
| HL-60 (Undifferentiated) | 0.11 ± 0.02 | 0.12 ± 0.02 |
| HL-60 (Retinoic acid-induced) | 0.73 ± 0.15 | 0.08 ± 0.02 |

Human red cells, lymphocytes, and platelets were isolated from peripheral blood as described under Methods. Undifferentiated HL-60 cells were grown in culture according to standard protocols. Differentiated HL-60 cells were obtained by exposing cells to 1 µM retinoic acid for 5 days in culture. After harvesting and isolation, all cells were kept in the standard medium for 1 hour at 37° C. prior to assay. The uptake of $[^3H]LXA_4$ was determined as in FIG. 1 (concentration=5 nM, time=1–30 min) and the influx rates in the presence and absence of 0.5 mM DISA were calculated as for FIG. 1. Results represent the means±SEM of three-four separate experiments for each cell type.

EXAMPLE 8

Release of $LXA_4$

Figure 7:
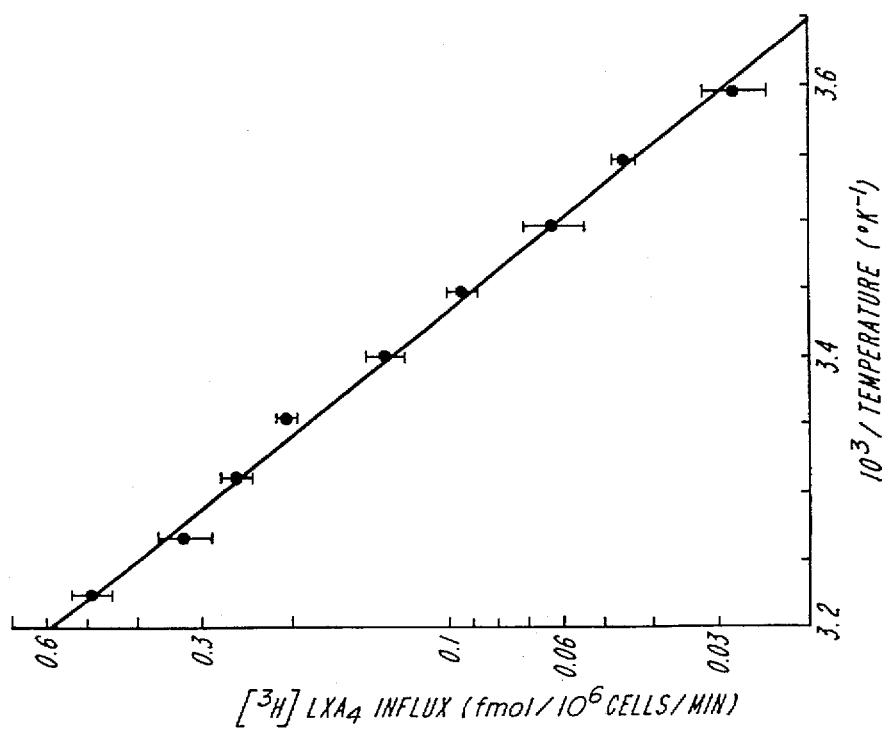
FIG. 7 is a graph depicting the Arrhenius plot of [$^3$H] $LXA_4$ influx into human neutrophils. The graph indicates a strictly linear relationship with no apparent breaks in the curve. The slope signifies an activation energy of 15.0±0.8 cal/mol.

"Efflux" kinetics are presented in FIG. 7. Cells were first labeled with $[^3H]LXA_4$ by incubating them with 5 nM $LXA_4$ for 15 min at 37° C. The cells were then pelleted and resuspended in the various experimental media, each in the absence of $LXA_4$. The loss of counts from the neutrophil pellet was followed over time. Results of three-four experiments are expressed as relative cell content, defined as cell-associated cpm at a given time divided by the starting cpm at zero-time. The curves represent declining single exponential fits to the individual sets of data. The parameters of the exponentials were as follows: for Control, rate coefficient=0.097±0.013 min$^{-1}$ and final value=0.54±0.03; for 0.5 mM DISA, 0.4 mM PCP, and $pH_o$ 8.40 (combined data set), rate coefficient 0.098±0.008 min$^{-1}$ and final value= 0.46±0.02; and for 0.5 mM mersalyl and $pH_o$ 6.40 (combined data), rate coefficient 0.079±0.012 min$^{-1}$ and final value=0.56±0.03.

It is immediately apparent that the principal mechanism underlying the loss of cell-associated $LXA_4$ is distinctly different from that for uptake. While at most only slight effects could be observed, none of the drugs tested or extremes of $pH_o$ (6.4–8.4) caused substantial changes in the off-rate. This implies that uptake and "efflux" signify two different phenomena. Conceivably, since none of the experimental maneuvers noted above altered receptor binding to any significant extent, it is quite possible that the loss of cell label actually represents dissociation from cell surface receptors. Moreover, $LXA_4$ that is translocated inward via the carrier to enter the cytosol may then preferentially partition into various membrane domains and organelles or become sequestered within hydrophobic compartments, thereby making it inaccessible to the plasma membrane-localized $LXA_4$ carrier. Some evidence for binding to nuclear and other cytoplasmic constituents has already been provided by subcellular fractionation studies (Fiore, S., et al., (1992) *J. Biol. Chem.* 267:16168–16176). One point, however, is clear: degradation of labeled $LXA_4$ cannot account for these findings as $LXA_4$ is not subject to metabolic transformation in neutrophils even at 37° C. (Fiore, S., et al., (1992) *J. Biol. Chem.* 267:116168–16176).

EXAMPLE 9

Effect of Lipoxins on Neutrophil Phagocytosis

When exposed to particulate material (e.g., red blood cell, microorganisms, crytals etc.), neutrophils ingest this particulate matter, a process termed phagocytosis. In this example, the ability of neutrophils to phagocytose opsonized sheep red blood cells was measured in the presence and in the absence of either $LXA_4$ or $LXB_4$.

Neutrophils were prepared as described in the general methodology and suspended at a concentration of $10\times10^6$–$15\times10^6$ cells/ml in Hepes Hanks buffer, pH 7.4, supplemented with 1 mg/ml BSA, 1 mg/ml glucose, 0.5 mM $MgCl_2$ and 1.0 mM $CaCl_2$—$2H_2O$.

The sheep red blood cells (SRBCs) were prepared by washing the cells with 1× veronal-buffered saline (VBS), incubating the cells with a 1:500 dilution of rabbit anti-SRBC IgG antibody at 37° C. for 15 minutes, centrifuging the cells at 2000 rpm for 5 minutes at 4° C. and washing the cells twice with 1×VBS. SRBCs were resuspended at a final concentration of $10\times10^8$ cells/ml.

For each phagocytosis reaction, a mixture was prepared which contained 25 µl of neutrophils (at $10\times10^6$–$15\times10^6$ cells/ml), an agent to be tested (e.g., $LXA_4$ or $LXB_4$ at final concentrations between 1 and 1000 nM) and media to a final volume of 100 µl. For control reactions, the agent to be tested (e.g., $LXA_4$ or $LXB_4$) was omitted. Each component was pipetted separately to the bottom of a 12×75 mm test tube to allow thorough mixing of the components.

To each 100 µl mixture was added 15 µl of opsonized SRBCs to start the phagocytosis reaction. The tubes were vortexed and placed in a 37° C. incubator for 30 minutes. After 30 minutes, the tubes were placed on ice to stop the reaction.

Non-phagocytosed SRBCs were lysed by adding 1.0 ml of 0.83% $NH_4Cl$ to each tube, with shaking, and centrifuging the tubes quickly at 1500 rpm for 3 minutes. The supernatant was removed and the pellets were resuspended in 30 gl of PBS. The 30 µl solution was placed onto a polylysine-coated microscope slide and after 15 minutes the excess solution was removed from the slide. The cells on the slide were fixed with 1% glutaraldehyde for 5 minutes and then the excess glutaraldehyde was removed. The cells were stained with Giemsa Stain by immersing the slide in the stain for 25 minutes, rinsing the slide with water and allowing the slide to dry overnight.

Figure 8:
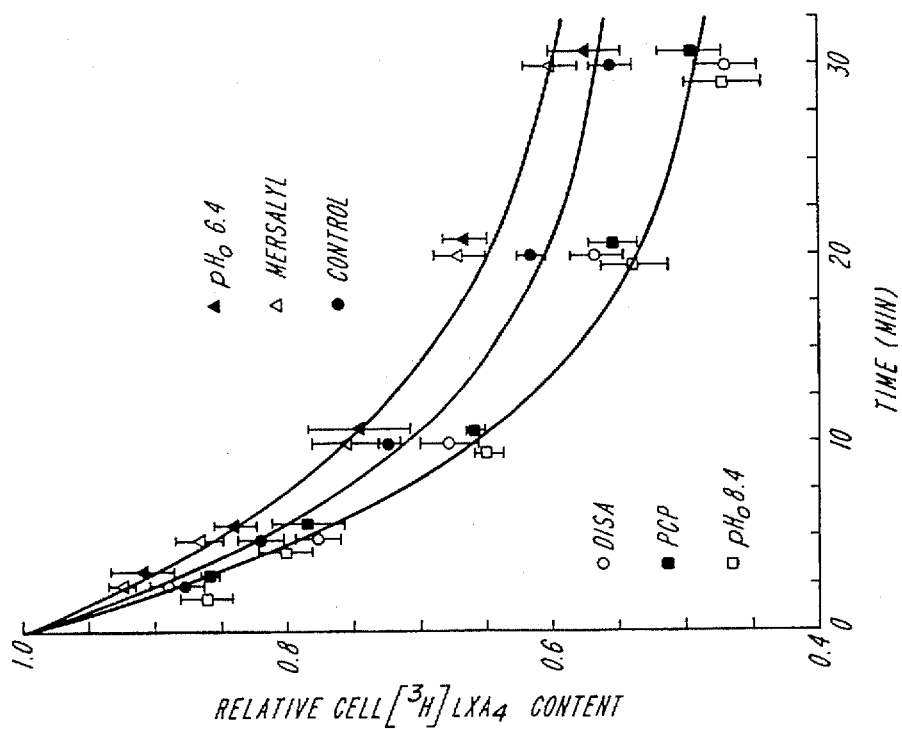
FIG. 8 is a graph depicting the time course of [$^3$H]$LXA_4$ efflux from neutrophils.

The slides were examined with a light microscope at 100×power. SRBCs which were phagocytosed by neutrophils were visible as yellow cells within blue-stained neutrophils. The results for each reaction were expressed as a phagocytic index, representing the number of SRBCs phagocytosed per 100 neutrophils. FIG. 8 shows a graph of the phagocytic index plotted against time for neutrophils incubated with media alone (control) or with 100 nM or 1000 nM $LXA_4$ or $LXB_4$. The results demonstrate that increasing amounts of lipoxin inhibit the phagocytic activity of neutrophils as measured by this assay. $LXA_4$ was more effective at inhibiting phagocytosis than $LXB_4$.

Figure 9:
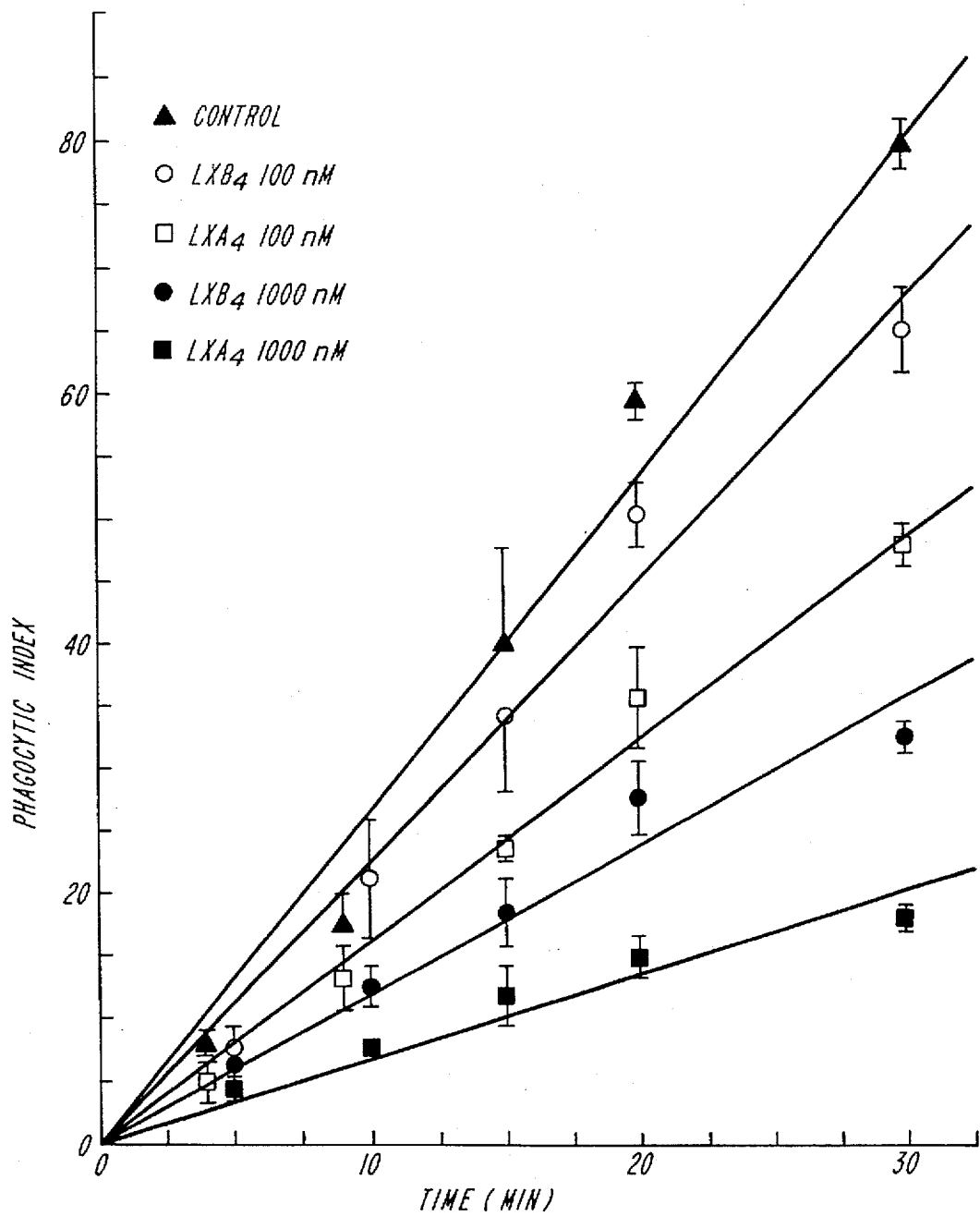
FIG. 9 is a graph depicting the effect of $LXA_4$ and $LXB_4$ on phagocytosis of opsonized sheep red blood cells by neutrophils.
Figure 10:
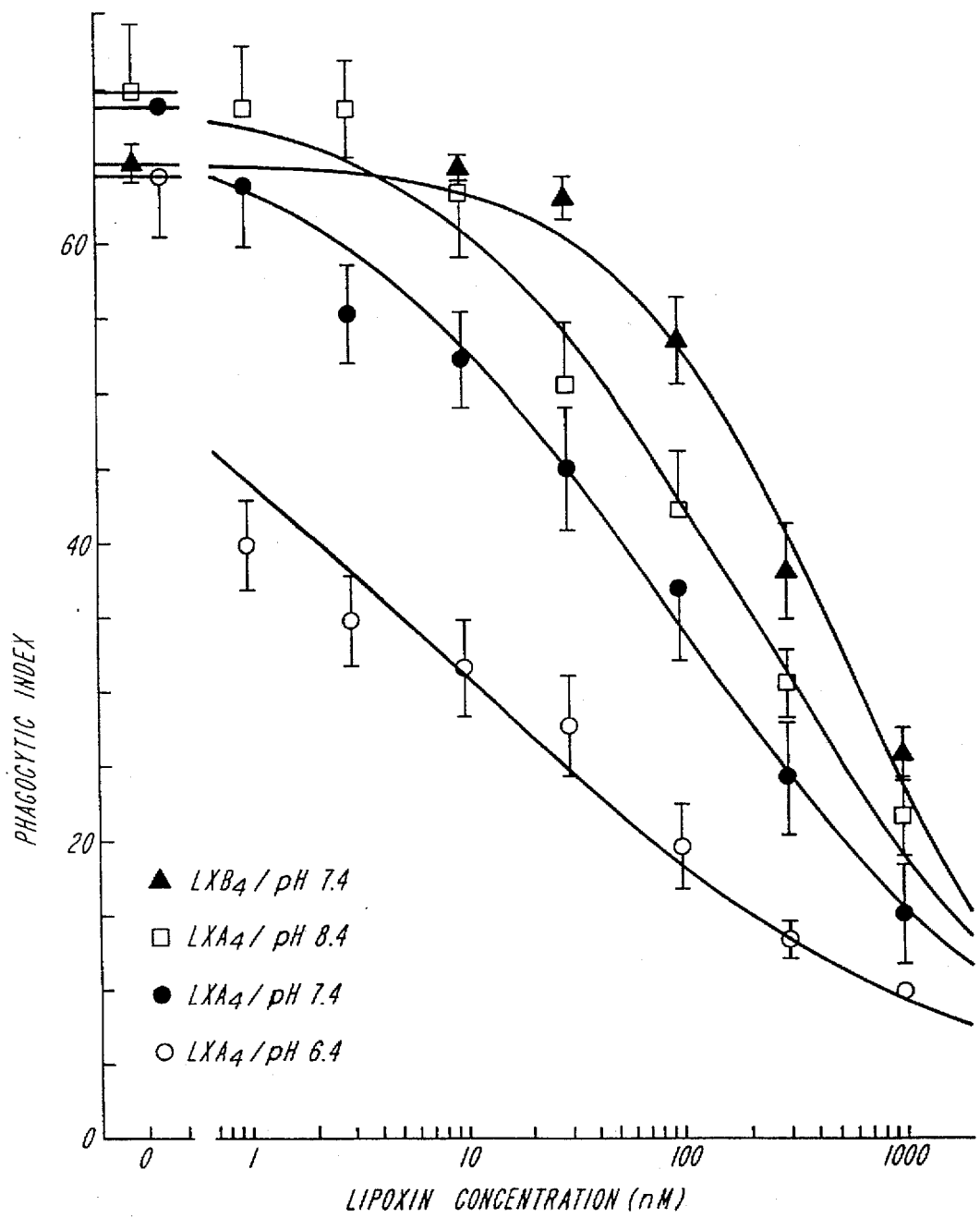
FIG. 10 is a graph depicting the effect of altering the extracellular pH on the inhibition of neutrophil-mediated phagocytosis by $LXA_4$.

To examine whether the inhibitory effect of $LXA_4$ on neutrophil phagocytosis was mediated by uptake of $LXA_4$ by the lipoxin transport system present on neutrophils, the effect of altering the pH on the ability of $LXA_4$ to inhibit phagocytosis was determined. Phagocytosis reactions similar to those described above were performed, except that in addition to performing the reactions at an extracellular pH of 7.4 (as described above), the extracellular pH was either decreased to pH 6.4 or increased to pH 8.4. The results are shown in FIG. 9, which depicts a graph of the phagocytic index plotted against lipoxin concentration. The results demonstrate that the ability of $LXA_4$ to inhibit neutrophil phagocytosis increases as the extracellular pH is decreased (i.e., as the acidity of the extracellular media is increased) and decreases as the extracellular pH is increased (i.e., as the acidity of the extracellular media is decreased). Thus, $LXA_4$-mediated inhibition of neutrophil phagocytosis exhibits pH-dependence. This pH dependence qualitatively resembles the pH-dependence of the lipoxin transport system, which also exhibits increased activity at pH 6.4 and decreased activity at pH 8.4. Therefore, the inhibition of neutrophil phagocytosis by $LXA_4$ is consistent with $LXA_4$ being taken up by the neutrophils via the lipoxin transport system.

EQUIVALENTS

Those skilled in the art will recognize, or be able to ascertain using no more than routine experimentation, numerous equivalents to the specific procedures described herein. Such equivalents are considered to be within the scope of this invention and are covered by the following claims.

We claim:

1. An in vitro method for inhibiting uptake of lipoxin $A_4$ by a cell which has a lipoxin transport system, comprising contacting the cell with a molecule which is an inhibitor of the lipoxin transport system.

2. The method of claim 1, wherein the inhibitor of the lipoxin transport system is an anion at physiological pH.

3. The method of claim 2, wherein the anion is selected from a group consisting of 3,5-diiodo-salicylic acid (DISA), pentachlorophenol (PCP) and α-cyano-β-(1-phenylindol-3-yl)acrylic acid (UK-5099).

4. The method of claim 1, wherein the inhibitor of the lipoxin transport system is an organomercurial agent.

5. The method of claim 4, wherein the organomercurial agent is mersalyl or p-hydroxymercuribenzoate (pHMB).

6. The method of claim 1 further comprising contacting the cell with a molecule which inhibits binding of lipoxin to a specific lipoxin receptor on the cell.

7. The method of claim 1, wherein the cell is selected from a group consisting of a neutrophil and a differentiated HL-60 cell.

8. An in vitro method for enhancing transport of a lipoxin into a neutrophil or differentiated HL-60 cell comprising contacting the neutrophil or differentiated HL-60 cell with a molecule which enhances transport of a lipoxin by the lipoxin transport system.

9. The method of claim 8, wherein the lipoxin is lipoxin $A_4$.

10. The method of claim 8, wherein the molecule which enhances transport of a lipoxin by the lipoxin transport system is n-formyl-methionylleucyl-phenylalanine.

11. The method of claim 8, wherein the molecule which enhances transport of a lipoxin by the lipoxin transport system is phorbol myristate acetate.

12. An in vitro method for inducing transport of a lipoxin into an undifferentiated HL-60 cell which can be induced to have a lipoxin transport system, comprising contacting the undifferentiated HL-60 cell with a molecule which induces transport of a lipoxin by the lipoxin transport system.

13. The method of claim 12, wherein the lipoxin is lipoxin $A_4$.

14. An in vitro method for modulating a response mediated by a lipoxin transport system in a neutrophil, comprising contacting the neutrophil with an enhancer of the lipoxin transport system to inhibit the response.

15. The method of claim 14, wherein the response is phagocytosis.

16. An in vitro method for modulating a response mediated by a lipoxin transport system in a neutrophil, comprising contacting the neutrophil with an inhibitor of the lipoxin transport system to stimulate the response.

17. The method of claim 16, wherein the response is phagocytosis.

18. An in vitro method for modulating a response mediated by a lipoxin transport system in a neutrophil, comprising contacting the neutrophil with an enhancer of the lipoxin transport system to stimulate the response.

19. An in vitro method for modulating a response mediated by a lipoxin transport system in a neutrophil, comprising contacting the neutrophil with an inhibitor of the lipoxin transport system to inhibit the response.

* * * * *